United States Patent
Pan

(10) Patent No.: US 8,765,791 B2
(45) Date of Patent: Jul. 1, 2014

(54) METHOD OF TREATING CANCER USING A NEUROPEPTIDE Y 5R (NP Y5R) ANTAGONIST

(75) Inventor: Guohua Pan, Oakville (CA)

(73) Assignee: University Health Network, Toronto (CA)

( * ) Notice: Subject to any disclaimer, the term of this patent is extended or adjusted under 35 U.S.C. 154(b) by 688 days.

(21) Appl. No.: 12/921,959

(22) PCT Filed: Mar. 10, 2009

(86) PCT No.: PCT/CA2009/000286
§ 371 (c)(1),
(2), (4) Date: Dec. 6, 2010

(87) PCT Pub. No.: WO2009/111868
PCT Pub. Date: Sep. 17, 2009

(65) Prior Publication Data
US 2011/0112102 A1    May 12, 2011

Related U.S. Application Data

(60) Provisional application No. 61/068,900, filed on Mar. 11, 2008, provisional application No. 61/126,909, filed on May 8, 2008, provisional application No. 61/190,356, filed on Aug. 28, 2008, provisional application No. 61/118,231, filed on Nov. 26, 2008.

(51) Int. Cl.
| | | |
|---|---|---|
| A01N 43/40 | (2006.01) | |
| A61K 31/44 | (2006.01) | |
| A01N 43/56 | (2006.01) | |
| A61K 31/415 | (2006.01) | |
| A01N 43/08 | (2006.01) | |
| A61K 31/34 | (2006.01) | |
| A01N 43/38 | (2006.01) | |
| A61K 31/40 | (2006.01) | |
| A01N 43/42 | (2006.01) | |
| C07D 405/00 | (2006.01) | |
| C07D 307/88 | (2006.01) | |
| C07D 237/02 | (2006.01) | |
| C07D 471/10 | (2006.01) | |
| A61K 31/4412 | (2006.01) | |
| A61K 31/4355 | (2006.01) | |

(52) U.S. Cl.
CPC ........... C07D 307/88 (2013.01); C07D 237/02 (2013.01); C07D 471/10 (2013.01); A61K 31/4412 (2013.01); A61K 31/4355 (2013.01)
USPC .......... 514/337; 514/407; 514/470; 514/410; 514/278; 546/284.1

(58) Field of Classification Search
CPC .. C07D 307/88; C07D 237/02; C07D 471/10; A61K 31/4412; A61K 31/4355
USPC ........ 514/337, 407, 470, 410, 278; 546/284.1
See application file for complete search history.

(56) References Cited

U.S. PATENT DOCUMENTS 4,914,105 A * 4/1990 Fujii et al. .................. 514/274
2002/0019389 A1   2/2002 Kim et al.
(Continued)

FOREIGN PATENT DOCUMENTS

CA    2379103       3/2001
WO    0114376 A1    3/2001
(Continued)

OTHER PUBLICATIONS

Qin et al. Mol. Cancer Ther. 2004, vol. 3, No. 3, pp. 247-259.*
Zakikhani et al. Cancer Res. 2006, vol. 66, pp. 10269-10273.*
Whiteman, H. Obesity linked to breast cancer cell growth and tumor size, Oct. 2013, pp. 1-3.*
DeCensi et al. American Society of Clinical Oncology, 2010, pp. 1-10.*
(Continued)

*Primary Examiner* — Samira Jean-Louis
(74) *Attorney, Agent, or Firm* — McCarter & English, LLP; Steven G. Davis; Wei Song

(57) ABSTRACT

The present invention relates to methods for treating cancer by administering a therapeutically effective amount of compound of formula (I), such as selective NPY5R antagonist MK-0557 (trans-N-[1-(2-fluorophenyl)-3-pyrazolyl]-3-oxospiro[6-azaisobenzofuran-1(3H), 1'-cyclohexane]-4'-carboxamide), or a pharmaceutically acceptable salt thereof, to a subject in need thereof The methods can further comprise administering a chemotherapeutic agent to the subject in need thereof.

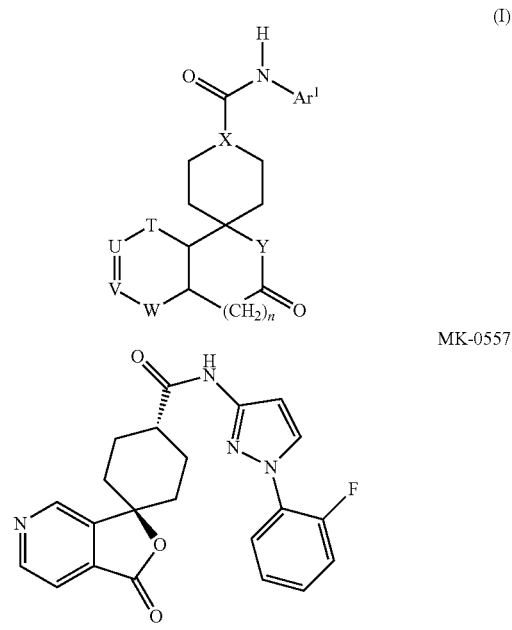

11 Claims, 25 Drawing Sheets

(56) References Cited

U.S. PATENT DOCUMENTS

2005/0288213 A1* 12/2005 MacNeil et al. ............... 514/2
2007/0099884 A1* 5/2007 Erondu et al. ............. 514/183

FOREIGN PATENT DOCUMENTS

WO  2004009015 A2  1/2004
WO  2004110375 A2  12/2004
WO  2007067781 A2  6/2007

OTHER PUBLICATIONS

Kitlinska et al., "Differential Effects of Neuropeptide Y on the Growth and Vascularization of Neural Crest-Derived Tumors", *Cancer Research*, vol. 65(5), pp. 1719-1728 (2005).
Ruscica et al., "Role of neuropeptide Y and its receptions in the progression of endocrine-related cancer", *Peptides*, vol. 28, pp. 426-434 (2007).
International Search Report for PCT Application No. PCT/CA2009/000286 dated Jun. 30, 2009.
Takeshi Nonaka et al., BIO Clinica, 2006, vol. 21, No. 13, p. 61-66.

* cited by examiner

FIG. 7 Selective NPY5R antagonists inhibit tube formation in an in vitro angiogenesis assay

| | | Number of tubes | |
|---|---|---|---|
| | | No NPY | Plus NPY |
| DMSO | | 20 | 24 |
| MK0557 | 1uM | 8 | 6 |
| | 10uM | 10 | 3 |

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
```

```
uaacacacau gcugucuucu u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uaauauggca caugacuuuu u                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uuacucucaa uucaugaacu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aacacuucga gaucucuuuu u                                              21
```

METHOD OF TREATING CANCER USING A NEUROPEPTIDE Y 5R (NP Y5R) ANTAGONIST

RELATED APPLICATIONS

This application is the U.S. National Stage of PCT/CA2009/000286, filed Mar. 10, 2009, which claims the benefit of U.S. Provisional Application No. 61/068,900, filed Mar. 11, 2008, U.S. Provisional Application No. 61/126,909, filed May 8, 2008, U.S. Provisional Application No. 61/190,356, filed Aug. 28, 2008, and U.S. Provisional Application No. 61/118,231, filed Nov. 26, 2008. The entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 29, 2010, is named 09811601.txt and is 1,399 bytes in size.

BACKGROUND OF THE INVENTION

Neuropeptide Y (NPY), a 36 amino acid peptide, is a sympathetic neurotransmitter and a potent orexigenic factor involved in the regulation of several aspects of neuroendocrine function and behavior, in particular food intake. (Heilig, M. and Widerlov, E., *Crit. Rev. Neurobiol.*, 9:115 (1995)). Five types of NPY receptors, Y1R, Y2R, Y4R, Y5R and Y6R have been characterized. It is thought that NPY exerts orexigenic functions mainly through its receptor subtypes: NPY1R and NPY5R. Several selective antagonists of NPY or its receptors have been developed and tested in vivo as anti-obesity agents. However, clinical trials designed to demonstrate the clinical efficacy of these antagonists in humans did not show clinically meaningful weight loss. For example, the selective NPY5R antagonist MK-0557 (trans-N-[1-(2-fluorophenyl)-3-pyrazolyl]-3-oxospiro[6 azaisobenzofuran-1 (3H), 1'-cyclohexane]-4'carboxamide) did not induce clinically meaningful weight loss in overweight or obese adults when administered at doses shown to result in receptor saturation (i.e., 1 mg/day, 5 mg/day or 25 mg/day). (Erondu, N. et al., *Obesity*, 15(4): 895-905 (2007)). Similarly, treatment with MK-0557 following very-low-calorie-diet induced weight loss did not result in a clinically meaningful reduction in weight regain. (Erondu, N. et al., *Obesity*, 15(4): 895-905 (2007)). Thus, antagonism of NPY5R is not an efficacious strategy for weight loss or control.

In addition to its role in promoting food intake and reducing energy expenditure, NPY has also been implicated in angiogenesis and in the growth of some tumor cells. NPY is present in a highly conserved manner across species, and is involved in several physiological responses and implicated in the pathophysiology of several disorders.

NPY is angiogenic and promotes growth for endothelial, vascular smooth muscle and neuronal cells. The angiogenic activity of NPY is mediated predominantly through NPY1R and NPY2R. NPY5R alone does not mediate angiogenesis, but NPY5R can act as an enhancer to augment angiogenesis mediated through NPY1R and/or NPY2R. (Ruscica, M. et al., *Peptides*, 28:426-434 (2007); Movafagh, S. et al., *FASEB J.*, 20(11):1924-1926 (2006)). Thus, a selective NPY5R antagonist would not be expected to inhibit angiogenesis or have efficacy in the treatment of an angiogenesis-mediated disease.

NPY and its cognate receptors, Y1R, Y2R and Y5R, are expressed in neural crest-derived tumors, however their role in regulation of tumor growth is unknown. Studies of the effect of NPY and NPY receptor antagonists on the growth and vascularization of neuroendocrine tumors have shown that an NPY5R antagonist blocked the mitogenic effect of NPY and decreased the number of viable SK-N-BE(2) neuroblastoma cells in an in vitro study. In contrast, the same NPY5R antagonist blocked the mitogenic effects of NPY, but increased the number of viable SK-N-MC Ewing's sarcoma cells, and significantly increased the number of viable PC12 pheochromocytoma cells in an in vitro study. (Kitlinska, J. et al., *Cancer Res.*, 65(5):1719-1728 (2005)). These findings demonstrate that the roles of NPY and its receptors in cancer remains to be elucidated.

A need exists to understand the role of NPY5R in cancer and other proliferative diseases, and for methods for treating of such conditions.

SUMMARY OF THE INVENTION

The invention provides methods for treating cancer in a subject in need thereof, using a selective NPY5R antagonist. As described herein, it has been discovered that compounds of Formula (I) (e.g., trans-N-[1-(2-fluorophenyl)-3-pyrazolyl]-3-oxospiro[6azaisobenzofuran-1(3H), 1'-cyclohexane]-4'carboxamide) directly induce death (e.g., apoptosis) and/or inhibit growth (e.g., proliferation) of tumor cells. Compounds of Formula (I) were taught to have anti-obesity activity, but the anti-tumor activity of these compounds was previously unknown.

As also described herein, it has been discovered that administration of an (one or more) NPY5R antagonist in combination with a (one or more) chemotherapeutic agent inhibits growth of tumor cells. In some embodiments, coadministration of an NPY5R antagonist and a chemotherapeutic agent produces a synergistic effect in inhibiting tumor growth. In a particular embodiment, a chemotherapeutic agent (for example, 200464 (also referred to as BI 2536, see U.S. Pat. No. 6,806,272, International Application No.: WO 03/020722 A1, and Steegmaier M. et al., *Current Biology* 17, 316-322 (2007), all of which are incorporated herein by reference), or 5-fluorouracil (5-FU)), and an NPY5R antagonist can be coadministered to inhibit tumor growth.

In one method of the invention, a therapeutically effective amount of a selective NPY5R antagonist having the structure of Formula (I):

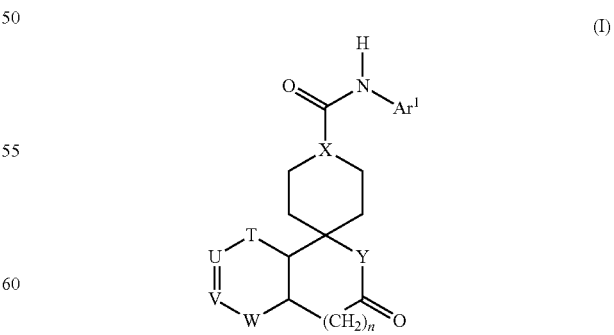

or a pharmaceutically acceptable salt thereof is administered to a subject in need thereof to treat cancer. In one aspect, the cancer is carcinoma, sarcoma, melanoma, fibrosarcoma, neuroblastoma, rabdomyosarcoma, lymphoma, myeloid cancer, endothelial cancer, epithelial cancer, breast cancer, cervical cancer, colon cancer, bladder cancer, skin cancer, prostate cancer, brain cancer, endometrial cancer, ovarian cancer, lung cancer or kidney cancer. In a preferred embodiment, the cancer is breast cancer, lung cancer, brain cancer, prostate cancer, or colon cancer. The method can further comprise administering a chemotherapeutic agent.

The invention also relates to a method of treating cancer in a subject in need thereof, comprising administering to the subject a therapeutically effective amount of trans-N-[1-(2-fluorophenyl)-3-pyrazolyl]-3-oxospiro[6 azaisobenzofuran-1(3H), 1'-cyclohexane]-4'carboxamide or a pharmaceutically acceptable salt thereof. In one aspect, the cancer is breast cancer, prostate cancer, lung cancer, brain cancer or colon cancer. In another aspect, trans-N-[1-(2-fluorophenyl)-3-pyrazolyl]-3-oxospiro[6 azaisobenzofuran-1(3H), 1'-cyclohexane]-4'carboxamide or a pharmaceutically acceptable salt thereof directly inhibits the growth of a tumor. The method can further comprise administering a chemotherapeutic agent.

The invention further relates to a method of inducing tumor death (e.g., apoptosis), comprising contacting the cells of the tumor with a compound of Formula (I) or a pharmaceutically acceptable salt thereof (e.g., trans-N-[1-(2-fluorophenyl)-3-pyrazolyl]-3-oxospiro[6 azaisobenzofuran-1(3H), 1'-cyclohexane]-4'carboxamide). In a preferred embodiment, the tumor is a breast tumor, a lung tumor, a brain tumor, a prostate tumor or a colon tumor. The method can further comprise administering a chemotherapeutic agent.

In a further aspect of the invention, the invention is a method of directly inhibiting tumor growth comprising administering to a subject in need thereof a therapeutically effective amount of a compound of Formula (I) or a pharmaceutically acceptable salt thereof (e.g., trans-N-[1-(2-fluorophenyl)-3-pyrazolyl]-3-oxospiro[6 azaisobenzofuran-1(3H), 1'-cyclohexane]-4'carboxamide). In a preferred embodiment, the tumor is a breast tumor, a lung tumor, a brain tumor, a prostate tumor or a colon tumor. The method can further comprise administering a chemotherapeutic agent.

The invention also relates to the use of a selective NPY5R antagonist of Formula (I) for the manufacture of a medicament for treating a cancer described herein, inducing tumor death or inhibiting tumor growth. The use can further comprise a chemotherapeutic agent.

The invention further relates to the use of a selective NPY5R antagonist of Formula (I) for treating a cancer described herein (e.g., breast cancer, lung cancer, brain cancer, prostate cancer, colon cancer), for inducing tumor death and for inhibiting tumor growth. The use can further comprise a chemotherapeutic agent. The invention relates to the combination of a selective NPY5R antagonist of Formula I and chemotherapeutic agent for use in treating a cancer as described herein, for inducing tumor death, or inhibiting tumor growth, or for inducing tumor regression. In one aspect, the invention relates to the use of trans-N-[1-(2-fluorophenyl)-3-pyrazolyl]-3-oxospiro[6 azaisobenzofuran-1 (3H), 1'-cyclohexane]-4'carboxamide and 200464 (BI 2536) for inhibiting tumor growth. In a further aspect, the invention relates to the use of trans-N-[1-(2-fluorophenyl)-3-pyrazolyl]-3-oxospiro[6 azaisobenzofuran-1(3H), 1'-cyclohexane]-4'carboxamide and 5-FU for inhibiting tumor growth.

DETAILED DESCRIPTION OF THE INVENTION

Figure 1:
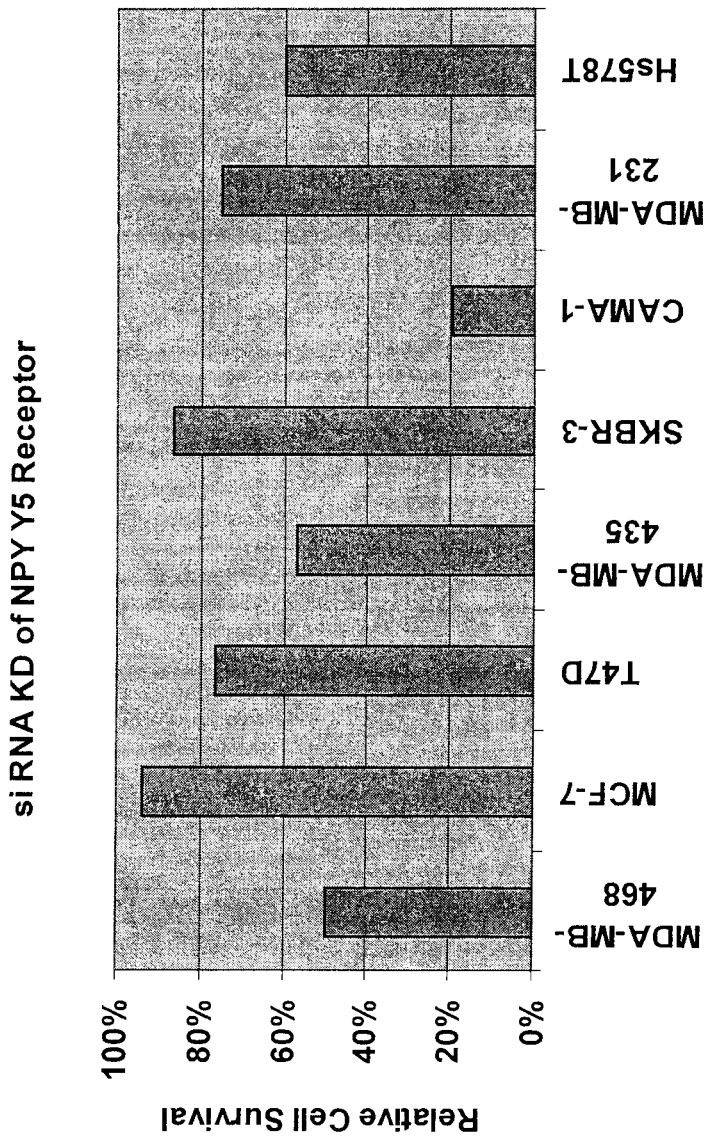
FIG. 1 is a bar graph illustrating siRNA knockdown of the NPY 5 receptor (NPY5R) and its effect on cell survival. The graph shows that depletion of NPY5R expression inhibits cancerous cell growth in a variety of breast cancer cell lines.

A description of example embodiments of the invention follows.

The invention provides methods for treating cancer in a subject in need thereof, using a selective NPY5R antagonist. The invention also provides methods for treating an angiogenesis-mediated disease (e.g., inhibiting angiogenesis) in a subject in need thereof using a selective NPY5R antagonist. As described herein, it has been discovered that compounds of Formula (I) (e.g., trans-N-[1-(2-fluorophenyl)-3-pyrazolyl]-3-oxospiro[6 azaisobenzofuran-1(3H), 1'-cyclohexane]-4'carboxamide) induce death and/or inhibit growth (e.g., proliferation) of tumor cells. As shown herein, selective antagonism of NPY5R in cancer cell lines using RNAi induced cell death, and the selective NPY5R antagonist trans-N-[1-(2-fluorophenyl)-3-pyrazolyl]-3-oxospiro[6 azaisobenzofuran-1(3H), 1'-cyclohexane]-4'carboxamide inhibited angiogenesis in an in vivo model and inhibited tumor growth in an in vivo model. Thus, selective antagonists of NPY5R have direct tumor killing activity and anti-angiogenic activity. One or both of these activities may contribute to the anti-tumor activity of trans-N-[1-(2-fluorophenyl)-3-pyrazolyl]-3-oxospiro[6 azaisobenzofuran-1(3H), 1'-cyclohexane]-4'carboxamide. Compounds of Formula (I) were taught to have anti-obesity activity, but the anti-tumor activity and anti-angiogenic activity of these compounds was previously unknown. Also shown herein is that an NPY5R antagonist and a chemotherapeutic agent can be coadministered to produce a synergistic effect in inhibiting tumor growth, thereby providing superior therapy, for example, for cancer or tumors. In a particular embodiment, the invention also provides a method of treating cancer (e.g., breast cancer) by administering a NYP5R antagonist (e.g., MK0557; (trans-N-[1-(2-fluorophenyl)-3-pyrazolyl]-3-oxospiro[6 azaisobenzofuran-1(3H), 1'-cyclohexane]-4'carboxamide)) in combination with a chemotherapeutic agent (e.g., 5-FU or 200464 (BI 2536).

Definitions

As used herein, "halogen atom" refers to fluorine atom, chlorine atom, bromine atom and iodine atom.

As used herein, "lower alkyl" refers to a straight- or branched-chain alkyl group of C1 to C6, for example, methyl, ethyl, propyl, isopropyl, butyl, isobutyl, sec-butyl, ter-butyl, pentyl, isopentyl, hexyl, isohexyl, and the like.

As used herein, "halo(lower)alkyl" refers to the aforesaid lower alkyl substituted with 1 or more, preferably 1 to 3 aforesaid halogen atoms identically or differently at the substitutable, arbitrary positions, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, and the like.

As used herein, "hydroxy(lower)alkyl" refers to the aforesaid lower alkyl substituted with 1 or more, preferably 1 or 2 hydroxy groups at the substitutable, arbitrary positions, for example, hydroxymethyl, 2-hydroxyethyl, 1-hydroxy-1-methylethyl, 1,2-dihydroxyethyl, 3-hydroxypropyl, and the like.

As used herein, "cyclo(lower)alkyl" refers to a cycloalkyl group of C3 to C6, for example, cyclopropyl, clyclobutyl, cyclopentyl, cyclohexyl, and the like.

As used herein, "lower alkenyl" refers to a straight- or branched-chain alkenyl group of C2 to C6, for example, vinyl, 1-propenyl, 2-propenyl, isopropenyl, 3-butenyl, 2-buenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl, and the like.

As used herein, "lower alkoxy" refers to a straight- or branched-chain alkoxy group of C1 to C6, for example, methoxy, ethoxy, propoxy, isopropoxy, butoxy, sec-butoxy, isobutoxy, tert-butoxy, penyloxy, isopentyloxy, hexyloxy, isohexyloxy, and the like.

As used herein, "halo(lower)alkoxy" refers to the aforesaid lower alkoxy substituted with 1 or more, preferably 1 to 3 aforesaid halogen atoms identically or differently at the substitutable, arbitrary positions, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy, and the like.

As used herein, "lower alkylthio" refers to a straight- or branched-chain alkylthio group of C1 to C6, for example, methylthio, ethylthio, propylthio, isopropylthio, butylthio, sec-butylthio, isobutylthio, tert-butylthio, pentylthio, isopentylthio, hexylthio, isohexylthio, and the like.

As used herein, "lower alkanoyl" refers to an alkanoyl group containing the aforesaid lower alkanoyl, that is, an alkanoyl group of C2 to C6, for example, acetyl, propionyl, butyryl, isobutyryl, valeryl, isovaleryl, pivaloyl, and the like.

As used herein, "lower alkoxycarbonyl" refers to an alkoxycarbonyl group containing the aforesaid lower alkoxycarbonyl, that is, an alkoxycarbonyl group of C2 to C6, for example, methoxycarbonyl, ethoxycarbonyl, propoxycarbonyl, isopropoxycarbonyl, butoxycarbonyl, tert-butoxycarbonyl, pentyloxycarbonyl, and the like.

As used herein, "lower alkylene optionally substituted with oxo" refers to a straight- or branched-chain alkylene group of C2 to C6 which may be substituted with 1 or more, preferably 1 oxo group at a substitutable, arbitrary position, for example, ethylene, trimethylene, tetramethylene, pentamethylene, hexamethylene, 1-oxoethylene, 1-oxotrimethylene, 2-oxotrimethylene, 1-oxotetramethylene, 2-oxotetramethylene, and the like.

As used herein, "aryl" includes phenyl, naphthyl, and the like.

As used herein, "heteroaryl" refers to 5- or 6-membered monocylic heteroaromatic group which contains 1 or more, preferably 1 to 3 hetero atoms identically or differently selected from the group of oxygen atom, nitrogen atom, and sulfur atom; or condensed heteroaromatic group, where the aforesaid monocylic heteroaromatic group is condensed with the aforesaid aryl group, or with the identified or different aforesaid monocylic heteroaromatic group each other, for example, pyrrolyl, furyl, thienyl, imidazolyl, pyrazolyl, thiazolyl, isothiazolyl, oxazolyl, isoxazolyl, 1,2,3-triazolyl, 1,2,4-triazolyl, tetrazolyl, oxadiazolyl, 1,2,3-thiadiazolyl, 1,2,4-thiadiazolyl, 1,3,4-thiadizolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, indazolyl, purinyl, quinolyl, isoquinolyl, phthalazyl, napthylidinyl, quinoxalinyl, quinazolinyl, cinnolinyl, pteridinyl, pyrido[3,2-b]pyridyl, and the like.

As used herein, "lower alkylamino" refers to an amino group mono-substituted with the aforesaid lower alkyl, for example, methylamino, ethylamino, propylamino, isopropylamino, butylamino, sec-butylamino, tert-butylamino, and the like.

As used herein, "di-lower alkylamino" refers to an amino group di-substituted with identical or different aforesaid lower alkyl, for example, dimethylamino, diethylamino, ethylmethylamino, dipropylamino, methylpropylamino, diisopropylamino, and the like.

In order to disclose the aforesaid compounds of the general Formula (I) in more detail, the various symbols used in the Formula (I) are explained with reference to preferred embodiments.

$Ar^1$ represents aryl or heteroaryl which may be substituted, the substituent being selected from the group consisting of halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by the formula -Q-$Ar^2$.

As used herein, "aryl or heteroaryl which may be substituted, the substituent being selected from the group consisting of halogen, nitro, lower alkyl, halo(lower) alkyl, hydroxy (lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of -Q-$Ar^2$" refers to unsubstituted aforesaid aryl or aforesaid heteroaryl, or the aforesaid aryl or aforesaid heteroaryl which has substitutent(s) at the substitutable, arbitrary position(s). The aforesaid substituent can be, identically or differently, one or more, preferably 1 or 2 selected from the group consisting of halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group of formula: -Q-$Ar^2$.

Halogen atom as the aforesaid substituent includes fluorine atom, chlorine atom, and the like preferably.

Lower alkyl as the aforesaid substituent includes methyl, ethyl, propyl, isopropyl, and the like preferably.

Halo(lower)alkyl as the aforesaid substituent includes difluoromethyl, trifluoromethyl, and the like preferably.

Hydroxy(lower)alkyl as the aforesaid substituent includes hydroxymethyl, 2-hydroxyethyl, 1-hydroxy-1-methylethyl, and the like preferably.

Cyclo(lower)alkyl as the aforesaid substituent includes cyclopropyl, cyclobutyl, and the like preferably.

Lower alkenyl as the aforesaid substituent includes vinyl, 1-propenyl, 2-methyl-1-propenyl, and the like preferably.

Lower alkoxy as the aforesaid substituent includes methoxy, ethoxy, and the like preferably.

Halo(lower)alkoxy as the aforesaid substituent includes fluoromethoxy, difluoromethoxy, trifluoromethoxy, and the like preferably.

Lower alkylthio as the aforesaid substituent includes methylthio, ethylthio, and the like preferably.

Lower alkanoyl as the aforesaid substituent includes acetyl, propionyl, and the like preferably.

Lower alkoxycarbonyl as the aforesaid substituent includes methoxycarbonyl, ethoxycarbonyl, and the like preferably.

Lower alkylene optionally substituted with oxo as the aforesaid substituent includes 1-oxotetramethylene, and the like preferably.

In a group of formula: -Q-$Ar^2$ as the aforesaid substituent, $Ar^2$ represents aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl;

Q represents a single bond or carbonyl.

As used herein, "aryl or heteroaryl which may be substituted, the substituent being selected from the group consisting of halogen, cyano, lower alkyl, halo(lower)alkyl, hydroxy (lower)alkyl, hydroxy, lower alkoxy, halo(lower)alkoxy, lower alkylamino, di-lower alkylamino, lower alkanoyl and aryl" refers to unsubstituted aforesaid aryl or aforesaid heteroaryl, or the aforesaid aryl or aforesaid heteroaryl which has substitutent(s) at the substitutable, arbitrary position(s). The aforesaid substituent can be, identically or differently, one or not less than 2, preferably 1 or 2 selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl.

Halogen atom as the aforesaid substituent includes, preferably, fluorine atom, chlorine atom, and the like.

Lower alkyl as the aforesaid substituent includes, preferably, methyl, ethyl, propyl, isopropyl, and the like.

Halo(lower)alkyl as the aforesaid substitutent includes, preferably, difluoromethyl, trifluoromethyl, and the like.

Hydroxy(lower)alkyl as the aforesaid substituent includes, preferably, hydroxymethyl, 2-hydroxyethyl, 1-hydroxy-1-methylethyl, and the like.

Lower alkoxy as the aforesaid substituent includes, preferably, methoxy, ethoxy, and the like.

Halo(lower)alkoxy as the aforesaid substituent includes, preferably, fluoromethoxy, difluoromethoxy, trifluoromethoxy, and the like.

Lower alkylamino as the aforesaid substituent includes, preferably, methylamino, ethylamino, and the like.

Di-lower alkylamino as the aforesaid substituent includes, preferably, dimethylamino, diethylamino, and the like.

Lower alkanoyl as the aforesaid substituent includes, preferably, acetyl, propionyl, and the like.

Aryl as the aforesaid substituent includes, preferably, phenyl, and the like.

The substituent(s) of $Ar^2$ include, preferably, halogen, cyano, lower alkyl, halo(lower)alkyl, hydroxy(lower)alkyl, hydroxy, halo(lower)alkoxy, and the like.

Aryl in $Ar^2$ includes, preferably, phenyl, and the like and heteroaryl includes imidazolyl, pyridyl, benzofuranyl, quinolyl, and the like.

Consequently, a group of formula: -Q-$Ar^2$ includes, for example, phenyl, 2-fluorophenyl, 3-fluorophenyl, 4-fluorophenyl, 2,3-difluorophenyl, 2,4-difluorophenyl, 3,5-difluorophenyl, 2-chlorophenyl, 3-chlorophenyl, 4-chlorophenyl, 2-cyanophenyl, 2-cyanophenyl, 3-cyanophenyl, 4-cyanophenyl, 2-methylphenyl, 3-methylphenyl, 4-methylphenyl, 2-fluoro-5-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 3-fluoro-5-methoxyphenyl, 3-fluoromethoxyphenyl, 3-difluoromethoxyphenyl, 3-(2-hydroxyethyl)phenyl, 3-hydroxymethylphenyl, 3-(1-hydroxy-1-methylethyl)phenyl, 3-hydroxyphenyl, 4-hydroxyphenyl, 2-imidazolyl, 1-ethyl-2-imidazolyl, 1,2,4-thiadiazol-5-yl, 1,3,4-thiadiaol-2-yl, 2-pyridyl, 3-pyridyl, 4-pyridyl, 2-ethyl-4-pyridyl, 4-pyrimidinyl, 5-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 8-quinolyl, benzoyl, 2-pyriylcarbonyl, and the like, and preferably, phenyl, 2-fluorophenyl, 3-fluorophenyl, 3,5-difluorophenyl, 3-chlorophenyl, 4-chlorophenyl, 3-cyanophenyl, 3-trifluoromethylphenyl, 3-difluoromethoxyphenyl, 3-(2-hydroxyethyl)phenyl, 3-hydroxyphenyl, 4-hydroxyphenyl, 1-ethyl-2-imidazolyl, 2-pyridyl, 7-benzo[b]furanyl, 2-quinolyl, 3-quinolyl, benzoyl, 2-pyridylcarbonyl, and the like.

The substituent of $Ar^1$ includes, preferably, halogen, lower alkyl, halo(lower)alkyl, lower alkenyl, lower alkanoyl, lower alkylene optionally substituted with oxo, and a group of formula: -Q-$Ar^2$, and the like.

Aryl in $Ar^1$ includes, preferably, phenyl, and the like and heteroaryl of $Ar^1$ includes pyrrolyl, imidazolyl, pyrazolyl, thiazolyl, oxazolyl, isoxazolyl, 1,2,3-triazolyl, 1,2,4-thiadiazolyl, pyridyl, pyrazinyl, pyrimidinyl, 1,2,4-triazinyl, benzoxazolyl, benzothiazolyl, quinolyl, pyrido[3,2-b]pyridyl, and the like.

Consequently, $Ar^1$ includes, for example, 3-fluorophenyl, 4-fluorophenyl, 3,4-difluorphenyl, 3-chlorophenyl, 4-chlorophenyl, 3,4-dichlorophenyl, 4-acetylphenyl, 5-oxo-5,6,7,8-tetrahydro-2naphthyl, 4-acetyl-3-trifluoromethylphenyl, 4-(1-ethyl-2-imidazolyl)phenyl, 3-(2-pyridyl)phenyl, 3-(4-pyridyl)phenyl, 4-(2-pyridyl)phenyl, 4-(3-pyridyl)phenyl, 4-(2-ethyl-4-pyridyl)phenyl, 4-(4-pyrimidinyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3-fluorophenyl)-4-imidazolyl, 1-(4-fluorophenyl)-4-imidazolyl, 1-(2,3-difluorophenyl)-4-imidazolyl, 1-(2,4-difluorophenyl)-4-imidazolyl, 1-(3,5-difluorophenyl)-4-imidazolyl, 1-(3-chlorophenyl)-4-imidazolyl, 1-(2-cyanophenyl)-4-imidazolyl, 1-(3-cyanophenyl)-4-imidazolyl, 1-(4-cyanophenyl)-4-imidazolyl, 1-(3-trifluoromethylphenyl)-4-imidazolyl, 1-[3-(1-hydroxy-1-methylethyl)phenyl]-4-imidazolyl, 1-(3-methoxyphenyl)-4-imidazolyl, 1-(2-difluoromethoxyphenyl)-4-imidazolyl, 1-(3-difluoromethoxyphenyl)-4-imidazolyl, 1-(4-difluoromethoxy-phenyl)-4-imidazolyl, 1-(2-pyridyl)-4-imidazolyl, 1-(4-benzo[b]furanyl)-4-imidazolyl, 1-(5-benzo[b]furanyl)-4-imidazolyl, 1-(7-benzo[b]furanyl)-4-imidazolyl, 1-(2-quinolyl)-4-imidazolyl, 1-(3-quinolyl)-4-imidazolyl, 1-(4-quinolyl)-4-imidazolyl, 1-(5-quinolyl)-4-imidazolyl, 1-(6-quinolyl)-4-imidazolyl, 1-(8-quinolyl)-4-imidazolyl, 1-phenyl-3-pyrazolyl, 5-phenyl-3-pyrazolyl, 1-phenyl-4-pyrazolyl, 1-(2-fluorophenyl)-3-pyrazolyl, 5-(2-fluorophenyl)-3-pyrazolyl, 5-(3-fluorophenyl)-3-pyrazolyl, 1-(3-fluorophenyl)-4-pyrazolyl, 1-(4-fluorophenyl)-3-pyrazolyl, 5-(4-fluorophenyl)-3-pyrazolyl, 5-(2-chlorophenyl)-3-pyrazolyl, 5-(3-chlorophenyl)-3-pyrazolyl, 5-(4-chlorophenyl)-3-pyrazolyl, 5-(2-difluoromethoxyphenyl)-3-pyrazolyl, 5-(3-difluoromethoxyphenyl)-3-pyrazolyl, 2-methyl-5-phenyl-3-pyrazolyl, 5-(2-pyridyl)-3-pyrazolyl, 5-(2-quinolyl)-3-pyrazolyl, 5-(3-quinolyl)-3-pyrazolyl, 4-phenyl-2-thiazolyl, 5-phenyl-2-thiazolyl, 5-(3-chlorophenyl)-2-thiazolyl, 5-(4-chlorophenyl)-2-thiazolyl, 5-(4-methoxyphenyl)-2-thiazolyl, 5-(2-pyridyl)-2-thiazolyl, 2-phenyl-4-thiazolyl, 4-phenyl-2-oxazolyl, 5-phenyl-2-oxazolyl, 4-(2-fluoromethoxyphenyl)-2-oxazolyl, 4-(3-fluoromethoxyphenyl)-2-oxazolyl, 5-phenyl-3-isoxazolyl, 3-phenyl-5-isoxazolyl, 3-(2-chlorophenyl)-5-isoxazolyl, 3-(3-chlorophenyl)-5-isoxazolyl, 3-(4-chlorophenyl)-5-isoxazolyl, 3-(2-pyridyl)-5-isoxazolyl, 2-phenyl-1,2,3-triazol-4-yl, 5-phenyl-1,2,4-thiadiazol-3-yl, 5-phenyl-1,3,4-thiadiazol-2-yl, 5-(3-chlorophenyl)-1,3,4-thiadiazol-2-yl, 5-(2-pyridyl)-1,3,4-thiadiazol-2-yl, 5-(2-ethyl-4-pyridyl)-1,3,4-thiadiazol-2-yl, 5-phenyl-2-pyridyl, 6-phenyl-3-pyridyl, 2-phenyl-4-pyridyl, 5-(2-pyridyl)-2-pyridyl, 5-benzoyl-2-pyridyl, 6-benzoyl-3-pyridyl, 5-chloro-2-pyrazinyl, 5-(2-methyl-1-propenyl)-2-pyrazinyl, 5-acetyl-2-pyrazinyl, 5-propionyl-2-pyrazinyl, 5-phenyl-2-pyrazinyl, 5-(3-hydroxyphenyl)-2-pyrazinyl, 5-(4-hydroxyphenyl)-2-pyrazinyl, 5-(1,2,4-thiadiazol-5-yl)-2-pyrazinyl, 5-(1,3,4-thiadiazol-2-yl)-2-pyrazinyl, 5-(2-pyridyl)-2-pyrazinyl, 5-(3-pyridyl)-2-pyrazinyl, 5-(5-pyrimidinyl)-2-pyrazinyl, 5-(3-quinolyl)-2-pyrazinyl, 5-benzoyl-2-pyrazinyl, 5-(2-pyridylcarbonyl)-2-pyrazinyl, 5-acetyl-2-pyrimidinyl, 6-phenyl-4-pyrimidinyl, 2-phenyl-5-pyrimidinyl, 5-(2-fluorophenyl)-2-pyrimidinyl, 5-(3-fluorophenyl)-2-pyrimidinyl, 5-(4-fluorophenyl)-2-pyrimidinyl, 5-(2-chlorophenyl)-2-pyrimidinyl, 5-(3-chlorophenyl)-2-pyrimidinyl, 5-(4-chlorophenyl)-2-pyrimidinyl, 5-(2-methylphenyl)-2-pyrimidinyl, 5-(3-methylphenyl)-2-pyrimidinyl, 5-(2-fluoromethylphenyl)-2-pyrimidinyl, 5-(3-fluoromethylphenyl)-2-pyrimidinyl, 5-(2-trifluoromethylphenyl)-2-pyrimidinyl, 5-(3-trifluoromethylphenyl)-2-pyrimidinyl, 5-(4-trifluoromethylphenyl)-2-pyrimidinyl, 5-(2-hydroxymethylphenyl)-2-pyrimidinyl, 5-(3-hydroxymethylphenyl)-2-pyrimidinyl, 5-(2-hydroxyphenyl)-2-pyrimidinyl, 5-(3-hydroxyphenyl)-2-pyrimidinyl, 5-(2-methoxyphenyl)-2-pyrimidinyl, 5-(3-methoxyphenyl)-2-pyrimidinyl, 5-(4-methoxyphenyl)-2-pyrimidinyl, 5-(2-fluoromethoxyphenyl)-2-pyrimidinyl, 5-(3-fluoromethoxyphenyl)-2-pyrimidinyl, 5-(2-fluoro-5-methylphenyl)-2-pyrimidinyl, 5-(3-fluoro-5-methoxyphenyl)-2-pyrimidinyl, 6-phenyl-3-pyridazinyl, 6-phenyl-1,2,4-triazin-3-yl, 5-chloro-2-benzoxazolyl, 5-fluoro-2-benzothiazolyl, 4-methyl-2-benzothiazolyl, 2-methyl-5-benzothiazolyl, 4-methoxy-2-benzothiazolyl, 3-quinolyl, 6-quinolyl, 7-methyl-2-quinolyl, 2-methyl-6-quinolyl, 6-chloro-2-quinoxalinyl, pyrido[3,2-b]pyridin-2-yl, 7-trifluoromethylpyrido[3,2-b]pyridin-2-yl, 7-difluoromethoxypyrido[3,2-b]pyridin-2-yl, 7-acetylpyrido[3,2-b]pyridin-2-yl, and the like, preferably, 3,4-dichlorophenyl, 4-acetylphenyl, 5-oxo-5,6,7,8-tetrahydro-2-naphthyl, 4-acetyl-3-trifluoromethylphenyl, 4-(1-ethyl-2-imidazolyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3,5-difluorophenyl)-4-imidazolyl, 1-(3-chlorophenyl)-4-imidazolyl, 1-(3-cyanophenyl)-4-imidazolyl, 1-[3-(2-hydroxyethyl)phenyl]-4-imidazolyl, 1-(3-difluoromethoxyphenyl)-4-imidazolyl, 1-(7-benzo[b]furanyl)-4-imidazolyl, 1-(2-quinolyl)-4-imidazolyl, 1-(3-quinolyl)-4-imidazolyl, 1-phenyl-3-pyrazolyl, 5-phenyl-3-pyrazolyl, 1-phenyl-4-pyrazolyl, 1-(3-fluorophenyl)-4-pyrazolyl, 1-(4-fluorophenyl)-3-pyrazolyl, 5-(4-chlorophenyl)-3-pyrazoly, 5-(3-quinolyl)-3-pyrazolyl, 5-phenyl-2-thiazolyl, 3-phenyl-5-isoxazolyl, 5-(2-methyl-1-propenyl)-2-pyrazinyl, 5-phenyl-2-pyrazinyl, 5-(3-hydroxyphenyl)-2-pyrazinyl, 5-(4-hydroxyphenyl)-2-pyrazinyl, 5-(2-pyridyl)-2-pyrazinyl, 5-benzoyl-2-pyrazinyl, 5-phenyl-2-pyrimidinyl, 5-(2-fluorophenyl)-2-pyrimidinyl, 5-(3-fluorophenyl)-2-pyrimidinyl, 5-(3-chlorophenyl)-2-pyrimidinyl, 5-(3-trifluoromethyl-phenyl)-2-pyrimidinyl, 5-chloro-2-benzoxazolyl, 4-methyl-2-benzothia-zolyl, 7-methyl-2-quinolyl, 7-trifluoromethylpyrido[3,2-b]pyridin-2-yl, and the like, especially 1-phenyl-3-pyrzolyl, 5-phenyl-3-pyrazolyl, 5-phenyl-2-pyrazinyl, 5-(3-hydroxyphenyl)-2-pyrazinyl, 5-(4-hydroxyphenyl)-2-pyrazinyl, 5-phenyl-2-pyrimidinyl, 5-(2-fluorophenyl)-2-pyrimidinyl, 5-(3-fluorophenyl)-2-pyrimidinyl, 7-trifluoro-methylpyrido[3,2-b]pyridin-2-yl, and the like.

n represents 0 or 1, 0 is preferable.

T, U, V and W represent independently nitrogen atom or methine, which may have a substituent selected from the group consisting of halogen, lower alkyl, hydroxy and lower alkoxy, where at least two of them represent the said methine group.

As used herein, "methine which may have a substituent selected from the group consisting of halogen, lower alkyl, hydroxy and lower alkoxy" refers to unsubstituted methine or methine having a substituent which can be selected from the group consisting of halogen, lower alkyl, hydroxy and lower alkoxy.

Halogen atom as the aforesaid substituent includes preferably fluorine atom, chlorine atom, and the like.

Lower alkyl as the aforesaid substituent includes preferably methyl, ethyl, and the like.

Lower alkoxy as the aforesaid substituent includes preferably methoxy, ethoxy, and the like.

The aforesaid substituent includes preferably halogen, and the like.

The preferred mode of T, U, V and W includes, for example, T, U, V and W are independently methine optionally having the aforesaid substituent, preferably halogen; or one of T, U, V and W is nitrogen atom.

X represents methine or nitrogen.

Y represents imino, which may be substituted with lower alkyl, or oxygen.

As used herein, "imino which may be substituted with lower alkyl" refers to unsubstituted imino or imino substituted with lower alkyl.

The aforesaid lower alkyl includes, preferably, methyl, ethyl, and the like.

Y is preferably unsubstituted imino or oxygen, especially oxygen.

As used herein, the term "pharmaceutically acceptable salts" refers to the pharmaceutically acceptable and common salts, for example, a base addition salt to carboxyl group when the compound has a carboxyl group, or an acid addition salt to amino or basic heterocyclyl when the compound has an amino or basic heterocyclyl group, including quaternary ammonium salts, prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollyarsanilate, sulfate, hexylresorcinate, subacetate, hydrabamine, succinate, hydrobromide, tannate, hydrochloride, tartrate, hydroxynaphthoate, teoclate, iodide, tosylate, trifluoro acetate, isothionate, triethiodide, lactate, panoate, valerate, and the like which can be used as a dosage form for modifying the solubility or hydrolysis characteristics or can be used in sustained release or pro-drug formulation.

"Pharmaceutically acceptable salts" include those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

As used herein, "subject" refers to an animal, preferably a mammal, most preferably a human. The term "subject in need thereof" refers to a subject who is in need of treatment or prophylaxis as determined by a researcher, veterinarian, medical doctor or other clinician. In one embodiment, a subject in need thereof is a mammal, such as a human. In another embodiment, a subject in need thereof is a cancer patient.

The need or desire for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

As used herein, "therapeutically effective amount" means an amount of the active compound that will elicit the desired biological or medical response in a tissue, system, subject, or human, which includes alleviation of the symptoms, in whole or in part, of the disorder being treated. The novel methods of treatment of this invention are for disorders known to those skilled in the art.

As used herein, "prophylactically effective amount" means an amount of the active compound that will elicit the biological or medical response in a tissue, system, subject, or human that is being sought to prevent the onset of cancer in a subject at risk of developing cancer.

As used herein "anti-tumor effective amount" means an amount sufficient to directly inhibit tumor cell growth (e.g., proliferation) or survival. For example, an amount sufficient to induce tumor apoptosis.

As used herein "anti-angiogenic effective amount" is an amount sufficient to inhibit angiogenesis.

As used herein, "directly inhibiting the growth of a tumor" means inhibiting tumor growth directly by inducing the death (e.g., apoptosis) of the cells of the tumor or by inhibiting the growth (e.g., proliferation) of the cells of the tumor.

As used herein a "selective NPY5R antagonist" is a compound that binds to and antagonizes NPY5R and has at least about 1000-fold selectivity for NPY5R relative to other NPY receptor subtypes. Preferred selective NPY5R antagonists have at least 2500-fold, at least 5000-fold, or at least 7500-fold selectivity for NPY5R relative to other NPY receptor subtypes. For example, a preferred selective NPY5R antagonist, trans-N-[1-(2-fluorophenyl)-3-pyrazolyl]-3-oxospiro[6 azaisobenzofuran-1(3H), 1'-cyclohexane]-4'carboxamide (MK-0557), has a Ki of 1.3 nM at human NPY5R, does not significantly bind human NPY1R, human NPY2R, human NPY4R or mouse NPY6R at a concentration of 10 µM, and has >7500-fold selectivity for NPY5R relative to other NPY receptor subtypes. (See, Erondu et al., *Cell Metabolism* 4:275-282 (2006).

As used herein a "chemotherapeutic agent" refers to an anticancer agent administered either before, during or after a primary cancer treatment (e.g., surgery, radiation) that assists in treating (e.g., eradicating cancer cells, containing cancer cells, inhibiting metastasis) a cancer. Examples of chemotherapeutic agents include alkylating agents (e.g., nitrogen mustard, nitrosoureas, alkyl sulfonates, triazines, ethylenimines), antimetabolites (e.g., 5-fluorouracil (5-FU), capecitabine, 6-mercaptopurine, metotrexate, gemcitabine, cytarabine, fludarabine, pemetrexed), anthracyclines (e.g., daunorubicin, doxorubicin, epirubicin, idarubicin), topoisomerase I or II inhibitors (e.g., topotecan, irinotecan, etoposide, teniposide), mitotic inhibitors (e.g., taxanes, epothilones, vinca alkaloids, estramustine), ATP-competitive inhibitors (e.g., polo-like kinase 1, 200464 (BI 2536)) and the like, and kinase inhibitors, including but not limited to mitotic kinases.

As defined herein, a "synergistic amount" or "synergistically effective amount" is an amount of two or more agents that produces greater than expected additive effect based on the mass-action law. A synergistic amount or synergistically effective amount has as combination index of less than one (CI <1). Preferably, the synergistic amount or synergistically effective amount has a CI of ≤0.85 (e.g., 0.7-0.85), ≤0.7 (e.g., 0.3-0.7), ≤0.3 (e.g., 0.1-0.3) or ≤0.1. The CI, method for calculating CI and plots useful for visualizing CI and synergistic, additive and antagonistic combinations are described in Chou, T-C., Theoretical Basis, Experimental Design, and Computerized Simulation of Synergism and Antagonism in Drug Combination Studies, *Pharmacological Reviews* 58(3): 621-681 (2006). The skilled addressee is directed, in particular, to section II regarding methods for calculating CI and plots useful for visualizing CI and synergistic, additive and antagonistic combinations. The entire teachings of Chou, T-C., Theoretical Basis, Experimental Design, and Computerized Simulation of Synergism and Antagonism in Drug Combination Studies, *Pharmacological Reviews* 58(3):621-681 (2006), including the portions specifically referred to herein, are incorporated herein by reference.

Methods of Therapy

The invention provides methods for treating cancer in a subject in need thereof, using a selective NPY5R antagonist. The invention also provides methods for treating cancer in a subject in need thereof, using a chemotherapeutic agent in combination with a selective NPY5R antagonist.

Accordingly, one aspect of the invention relates to a method for treating cancer (e.g., breast cancer, lung cancer, prostate cancer, brain cancer, colon cancer) in a subject, comprising administering to the subject a therapeutically effective amount of a selective NPY5R antagonist of Formula (I):

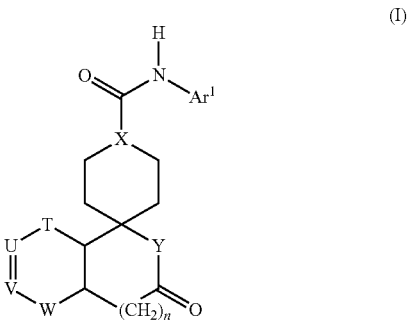

or a pharmaceutically acceptable salt thereof, wherein:
$Ar^1$ is selected from the group consisting of:
(1) aryl, and
(2) heteroaryl,
wherein the aryl and heteroaryl groups are unsubstituted or optionally substituted with a substituent selected from the group consisting of (a) halogen,
(b) nitro,
(c) lower alkyl,
(d) halo(lower)alkyl,
(e) hydroxy(lower)alkyl,
(f) cyclo(lower)alkyl,
(g) lower alkenyl,
(h) lower alkoxy,
(i) halo(lower)alkoxy,
(j) lower alkylthio,
(k) carboxyl,
(l) lower alkanoyl,
(m) lower alkoxycarbonyl,
(n) lower alkylene optionally substituted with oxo, and
(o) -Q-Ar$^2$;
Ar$^2$ is selected from the group consisting of
(1) aryl, and
(2) heteroaryl,
wherein aryl and heteroaryl are unsubstituted or optionally substituted with a substituent selected from the group consisting of:
(a) halogen,
(b) cyano,
(c) lower alkyl,
(d) halo(lower)alkyl,
(e) hydroxy(lower)alkyl,
(f) hydroxy,
(g) lower alkoxy,
(h) halo(lower( )alkoxy,
(i) lower alkylamino,
(j) di-lower alkylamino,
(k) lower alkanoyl, and
(l) aryl;
n is 0 or 1;
Q is selected from the group consisting of a single bond or carbonyl;
T, U, V and W are each independently selected from the group consisting of
(1) nitrogen, and
(2) methine,
wherein the methine group is unsubstituted or optionally substituted with a substituent selected from the group consisting of:
(a) halogen,
(b) lower alkyl,
(c) hydroxy, and
(d) lower alkoxy; and
wherein at least two of T, U, V, and W are methine;
X is selected from the group consisting of
(1) nitrogen, and
(2) methine; and
Y is selected from the group consisting of
(1) imino, unsubstituted or optionally substituted with lower alkyl, and
(2) oxygen.
In preferred compounds of Formula (I), T, V, W and X are methine, U is nitrogen, n is 0 and Y is oxygen.
A preferred selective NPY5R antagonist of Formula (I) is trans-N-[1-(2-fluorophenyl)-3-pyrazolyl]-3-oxospiro[6 azaisobenzofuran-1(3H), 1'-cyclohexane]-4'-carboxamide, also known as MK-0557.

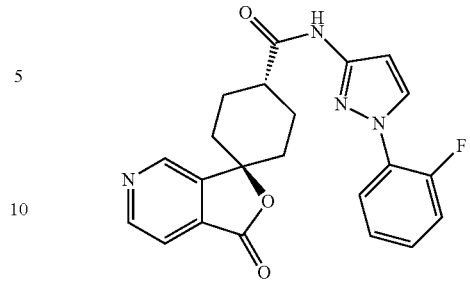

MK-0557

In preferred methods of the invention, cancer can be treated, for example tumor growth can be inhibited (e.g., directly inhibited) using the selective NPY5R antagonist trans-N-[1-(2-fluorophenyl)-3-pyrazolyl]-3-oxospiro[6 azaisobenzofuran-1(3H), 1'-cyclohexane]-4'carboxamide or a pharmaceutically acceptable salt thereof.

Suitable methods for preparing compounds of Formula (I), including MK-0557, are disclosed in U.S. Pat. No. 6,335,345 B1 (columns 19-30 and Examples 62-(6) and 101, for example) and WO 2007/016028 (Examples 1-4, for example). The entire disclosures of U.S. Pat. No. 6,335,345 B1 and WO 2007/016028 are incorporated herein by reference.

Accordingly, one aspect of the invention relates to a method for treating cancer or a tumor in a subject comprising administering to the subject a therapeutically effective amount of trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof, to the subject.

The cancer or tumor treated using the method of the invention can be any cancer (e.g., carcinoma, sarcoma, melanoma, fibrosarcoma, neuroblastoma, rabdomyosarcoma, lymphoma (e.g., Hodgkin's Lymphoma), myeloid, endothelial, epithelial, breast, cervical, colon, bladder, skin, prostate, brain, kidney, ovarian, endometrial) or particular type of tumor (e.g., primary breast tumor, nodal breast tumor, lung tumor, brain tumor, colon tumor, prostate tumor) which expresses NPY5R. In a particular embodiment, the subject has a breast, prostate, lung, brain or colon tumor which expresses NPY5R.

In a particular embodiment of the invention, the method of treating cancer (e.g. breast cancer, prostate cancer, lung cancer, brain cancer, colon cancer) in a subject comprises administering to the subject a therapeutically effective amount of trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof.

In other embodiments, the invention is a method for directly inhibiting the growth of a tumor that expresses NPY5R, comprising administering to a patient with the tumor a therapeutically effective amount (e.g., an anti-tumor effective amount) of a selective NPY5R antagonist of Formula (I). In one embodiment, the NPY5R antagonist is trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof.

In other embodiments, the invention is a method for inducing tumor death, comprising administering to a patient with the tumor a therapeutically effective amount (e.g., an anti-tumor effective amount) of a selective NPY5R antagonist of Formula (I). In one embodiment, the NPY5R antagonist is trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof.

Another aspect of the invention relates to the use of a selective NPY5R antagonist of Formula (I) for the manufacture of a medicament for treating cancer (e.g., breast cancer, lung cancer, prostate cancer, brain cancer, colon cancer or other cancer described herein), inducing tumor death (e.g., apoptosis), or inhibiting tumor growth.

The invention further relates to the use of a selective NPY5R antagonist of Formula (I) for treating cancer (e.g., breast cancer, lung cancer, prostate cancer, brain cancer, colon cancer or other cancer described herein), inducing tumor death (e.g., apoptosis) or inhibiting tumor growth.

As shown herein, the selective NPY5R antagonist trans-N-[1-(2-fluorophenyl)-3-pyrazolyl]-3-oxospiro[6 azaisobenzofuran-1(3H), 1'-cyclohexane]-4'carboxamide inhibited angiogenesis in an in vivo model. Thus, similar to the use of other known anti-angiogenic agents, selective antagonists of NPY5R can be used to treat angiogenesis mediated diseases. For example, Avastin® (bevacizumab, Genentech), a recombinant humanized antibody that binds and inhibits vascular endothelial growth factor (VEGF), a protein involved in the pathogenesis of macular degeneration (Kliffen, M., et al., *British Journal of Ophthalmology*, 81:154-162 (1997); Churchill, A J., et al., *Human Molecular Genetics*, 15(19): 2955-2961 (2006)), has been shown to be useful in the treatment of age-related macular degeneration (Emerson M V, et al., *Retina*, 27(4):439-444 (2007); Goff, M J., et al., *Retina*, 27(4):432-438 (2007); Emerson, M V., et al., *Retina*, 27(4): 439-444 (2007); Pederson, K B, et al., *Acta Ophthamology* (Dec. 16, 2008)).

Accordingly, in other embodiments, the invention is a method for inhibiting angiogenesis, or treating an angiogenesis mediated disease, comprising administering to a patient a therapeutically effective amount (e.g., an anti-angiogenic effective amount) of a selective NPY5R antagonist of Formula (I). In one embodiment, the NPY5R antagonist is trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof. In some embodiments, the invention is a method for treating an angiogenesis-mediated disease selected from the group consisting of cancer, diabetic blindness, age-related macular degeneration, inflammatory bowel disease, sarcoidosis, rheumatoid arthritis and psoriasis. In a particular embodiment, the invention is a method for treating age-related macular degeneration.

Another aspect of the invention relates to the use of a selective NPY5R antagonist of Formula (I) for the manufacture of a medicament for treating an angiogenesis-mediated disease (e.g., cancer, diabetic blindness, age-related macular degeneration, inflammatory bowel disease, sarcoidosis, rheumatoid arthritis and psoriasis).

The invention further relates to the use of a selective NPY5R antagonist of Formula (I) for treating an angiogenesis-mediated disease (e.g., cancer, diabetic blindness, age-related macular degeneration, inflammatory bowel disease, sarcoidosis, rheumatoid arthritis and psoriasis).

Many anti-cancer therapeutics (e.g., targeted cancer therapeutics) are administered in conjunction with one or more other therapeutic agents and/or treatment regimens. For example, a therapeutic agent used as an adjuvant therapy can be administered as a secondary therapy to some primary cancer therapy. Adjuvant therapies include, for example, chemotherapies (e.g., dacarbazine (DTIC), Cis-platinum, cimetidine, tamoxifen, cyclophophamide), hormone (endocrine) therapies (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene)) and radiation therapy. Radiation therapy can be used as both a primary and adjuvant therapy. Although occasionally used alone, these therapies are typically used as adjuvants, that is, in addition to primary cancer treatments such as the surgical removal of tumors, radiation therapy or antibody therapy (e.g., a monoclonal antibody administered alone and/or conjugated to a cytotoxic agent (e.g., ricin)). Numerous other therapies can also be administered during a cancer treatment regime to mitigate the effects of the disease and/or side effects of the cancer treatment including therapies to manage pain (narcotics, acupuncture), gastric discomfort (antacids), dizziness (anti-vertigo medications), nausea (anti-nausea medications), infection (e.g., medications to increase red/white blood cell counts) and the like.

Thus, a selective NPY5R antagonist can be administered as an adjuvant therapy (e.g., with another primary cancer therapy or treatment). As an adjuvant therapy, a selective NPY5R antagonist can be administered before, after or concurrently with a primary therapy such as radiation and/or the surgical removal of a tumor(s).

In some embodiments, the methods described herein can further comprise administering a therapeutically effective amount of a selective NPY5R antagonist and one or more other therapies (e.g., adjuvant therapies, other targeted therapies). As shown herein, coadministration of an NPY5R antagonist and a chemotherapeutic agent can produce a synergistic effect in inhibiting tumor growth, thereby providing superior therapy, for example, for cancer or tumors.

Accordingly, in the methods of the invention, the NPY5R antagonist is administered in combination with a chemotherapeutic agent. In a particular embodiment, the chemotherapeutic agent is 5-FU. In another aspect, the chemotherapeutic agent is 200464 (BI 2536), an ATP competitive inhibitor that inhibits PLK1 (polo-like kinase 1). 200464 (BI 2536) can cause mitotic arrest. In yet another embodiment, the cancer is breast cancer.

In one aspect of the invention relates to a method for treating cancer or a tumor in a subject comprising administering to the subject a therapeutically effective amount of trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof, and a chemotherapeutic agent to the subject.

In a particular embodiment of the invention, the method of treating cancer (e.g. breast cancer, prostate cancer, lung cancer, brain cancer, colon cancer) in a subject comprises administering to the subject a therapeutically effective amount of trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof and a chemotherapeutic agent.

In other embodiments, the invention is a method for directly inhibiting the growth of a tumor that expresses NPY5R, comprising administering to a patient with the tumor a therapeutically effective amount (e.g., an anti-tumor effective amount) of a selective NPY5R antagonist of Formula (I). In one embodiment, the NPY5R antagonist is trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof and a chemotherapeutic agent.

In other embodiments, the invention is a method for inducing tumor death, comprising administering to a patient with the tumor a therapeutically effective amount (e.g., an anti-tumor effective amount) of a selective NPY5R antagonist of Formula (I). In one embodiment, the NPY5R antagonist is trans-N-[1-(2-fluorophenyl)-3-pyrazolyl]-3-oxospiro[6 azaisobenzofuran-1(3H), 1'-cyclohexane]-4'carboxamide, or a pharmaceutically acceptable salt thereof and a chemotherapeutic agent.

Another aspect of the invention relates to the use of a selective NPY5R antagonist of Formula (I) and a chemotherapeutic agent for the manufacture of a medicament for treating cancer (e.g., breast cancer, lung cancer, prostate cancer, brain cancer, colon cancer or other cancer described herein), inducing tumor death (e.g., apoptosis), or inhibiting tumor growth.

The invention further relates to the use of a selective NPY5R antagonist of Formula (I) and a chemotherapeutic agent for treating cancer (e.g., breast cancer, lung cancer, prostate cancer, brain cancer, colon cancer or other cancer described herein), inducing tumor death (e.g., apoptosis) or inhibiting tumor growth.

An adjuvant therapy (e.g., a chemotherapeutic agent) and/or the one or more other targeted therapies and a NPY5R antagonist can be co-administered simultaneously (i.e., concurrently) as either separate formulations or as a joint formulation. Alternatively, the therapies can be administered sequentially, as separate compositions, within an appropriate time frame (e.g., a cancer treatment session/interval (e.g., about 1.5 to about 5 hours to about 10 hours to about 15 hours to about 20 hours; about 1 day to about 2 days to about 5 days to about 10 days to about 14 days)) as determined by the skilled clinician (e.g., a time sufficient to allow an overlap of the pharmaceutical effects of the therapies). The adjuvant therapy and/or one or more other targeted therapies and a NPY5R antagonist can be administered in a single dose or multiple doses in an order and on a schedule suitable to achieve a desired therapeutic effect (e.g., inhibition of tumor growth).

In one embodiment, first the chemotherapeutic agent is administered, then the NPY5R antagonist is administered to the subject in need thereof. In a particular embodiment, the chemotherapeutic agent is administered (e.g., for about 1 day, 2 days, 3 days, 4 days, 5 days, 6 days, 7 days (1 week), 8 days, 9 days, 10 days, 11 days, 12 days, 13 days, 14 days (2 weeks), etc.), and then the NPY5R antagonist is administered (e.g., for about 1 day, 2 days, 3 days, 4 days, 5 days, 6 days, 7 days (1 week), 8 days, 9 days, 10 days, 11 days, 12 days, 13 days, 14 days (2 weeks), 15 days, 16 days, 17 days, 18 days, 19 days, 20 days, 21 days (3 weeks), etc.) to the subject in need thereof. In a particular embodiment, the chemotherapeutic agent is administered every days for 5 days and then the chemotherapeutic agent is administered 3 times a week for about 3 weeks.

When administered to treat an angiogenesis-mediated disease, the selective NPY5R antagonist can be administered with another therapeutic agent, such as the agent that targets a different pathological process involved in the disease. Examples of suitable therapeutic agents that can be administered with a selective NPY5R antagonist to treat an angiogenesis-mediated disease include 5-ASA, sulfasalazine (Azulfadine), mesalamine (Asacol®, Pentasa®), azathioprine (Imuran®), 6-MP (Purinethol®), cyclosporine, methotrexate, infliximab (Remicade®), corticosteroids (prednisone, prednisolone, cortisone), ranibizumab (Lucentis®), pegaptanib sodium, verteporfin (Visudyne®), hydroxychloroquine, chloroquine, methotrexate, mycophenolate mofetil, azathioprine, cyclophosphamide, etanercept, adalimumab, thalidomide, pentoxifylline, tetracyclines (e.g., minocycline, doxycycline), etanercept (Enbrel®), alefacept (Amevive®), efalizumab (Raptiva®), and adalimumab (Humira®).

The methods of the invention also include treating cancer and/or inhibiting angiogenesis with alternative forms of compounds of Formula (I), such as isomers, including stereoisomers such as optical isomers, enantiomers and/or diastereomers and geometrical isomers, or tautomers depending upon the mode of substituents of Formula (I).

Suitable crystal forms of compounds of Formula (I) (e.g., (trans-N-[1-(2-fluorophenyl)-3-pyrazolyl]-3-oxospiro[6 azaisobenzofuran-1(3H), 1'-cyclohexane]-4'carboxamide) are disclosed in WO 2007/016028, published Feb. 8, 2007. The disclosures of WO 2007/016028 are incorporated herein by reference and provide examples of suitable crystal forms that can be administered in the methods of the invention.

A therapeutically effective amount of a compound of Formula (I) (e.g., trans-N-[1-(2-fluorophenyl)-3-pyrazolyl]-3-oxospiro[6 azaisobenzofuran-1(3H), 1'-cyclohexane]-4'carboxamide) is administered in the methods of the invention. Suitable dosing schedules and amounts for a NPY5R antagonist can be readily determined by a clinician of ordinary skill and may vary depending on the relative potency of the individual antagonist, the delivery means, and various patient factors, such as age, weight, sex, sensitivity or tolerance to drugs, and overall well-being. In general, dosage is from 0.01 mg to 1 g per kg of body weight, and may be given repeated after a suitable interval, for example once or more daily, weekly, monthly or yearly. The clinician can determine repetition rates for dosing based on measured residence times, concentrations of the drug in bodily fluids or tissues or other parameters. Decreased toxicity of a selective NPY5R antagonist as compared to chemotherapeutic agents can allow for the time between administration cycles to be shorter. Following successful treatment, it may be desirable to have the patient undergo maintenance therapy to prevent the recurrence of the disease state, wherein the antagonist is administered in maintenance doses, ranging from about 0.01 µg to about 1 g, preferably from about 0.01 µg to about 50 mg per kg of body weight, at a suitable interval, such as daily, biweekly, monthly, or semiannually. When used as an adjuvant therapy (to, e.g., surgery, radiation therapy, other primary therapies), a selective NPY5R antagonist is preferably administered on a dosing schedule that is similar to that of the other cancer therapy (e.g., chemotherapeutics), or on a dosing schedule determined by the skilled clinician to be more/most effective at inhibiting (e.g., reducing, preventing) tumor growth.

In one aspect, an "anti-tumor effective amount" or "anti-angiogenic effective amount" of a NPY5R antagonist is administered to a patient in need thereof. Generally, an anti-tumor effective amount or anti-angiogenic effective amount is greater than an amount believed to be suitable for treating obesity, stopping weight gain or causing weight loss. For example, in general, an anti-tumor effective amount or anti-angiogenic effective amount is generally more than 1 mg/day, more than 5 mg/day or more than 25 mg/day.

In one example of an anti-tumor effective amount, the maximum tolerated dose is administered during a relatively short treatment period (e.g., one to several days), which is followed by an off-therapy period. For example, an antagonist can be administered in a first cycle in which the maximum tolerated dose of the antagonist is administered in one dose, or in several doses administered after closely spaced intervals (minutes, hours, days) with a subsequent cycle administered after a suitable off-therapy period (e.g., one or more weeks), if desired.

In another example, a selective NPY5R antagonist (e.g., trans-N-[1-(2-fluorophenyl)-3-pyrazolyl]-3-oxospiro[6 azaisobenzofuran-1(3H), 1'-cyclohexane]-4'carboxamide) can be administered in a metronomic dosing regime, whereby a lower dose is administered more frequently relative to maximum tolerated dosing. A number of preclinical studies have demonstrated superior anti-tumor efficacy, potent anti-angiogenic effects, and reduced toxicity and side effects (e.g., myelosuppression) of metronomic regimes compared to maximum tolerated dose (MTD) counterparts (Bocci et al., Cancer Res, 62:6938-6943, (2002); Bocci et al., Proc. Natl. Acad. Sci., 100(22):12917-12922, (2003); and Bertolini et al., Cancer Res, 63(15):4342-4346, (2003)). Metronomic chemotherapy appears to be effective in overcoming some of the major shortcomings associated with chemotherapy.

The selective NPY5R antagonist (e.g., compound of Formula (I), trans-N-[1-(2-fluorophenyl)-3-pyrazolyl]-3-oxospiro[6 azaisobenzofuran-1(3H), 1'-cyclohexane]-4'carboxamide) can be administered to a subject as part of a pharmaceutical composition. Formulations or compositions comprising a selective NPY5R antagonist or compositions comprising a selective NPY5R antagonist and one or more targeted therapies will vary according to the route of administration selected (e.g., solution, emulsion or capsule). A "pharmaceutical composition" comprises a selective antagonist of NPY5R (e.g., compound of Formula (I), trans-N-[1-(2-fluorophenyl)-3-pyrazolyl]-3-oxospiro[6 azaisobenzofuran-1(3H), 1'-cyclohexane]-4'carboxamide) as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Any suitable route of administration can be used, for example, oral, dietary, topical, transdermal, rectal, parenteral (e.g., intravenous, intraarterial, intramuscular, subcutaneous injection, intradermal injection), inhalation (e.g., intrabronchial, intranasal or oral inhalation, intranasal drops), ocular, pulmonary, nasal, and the like may be employed. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like.

For administration by inhalation, the compositions of the present invention are conveniently delivered in the form of an aerosol spray presentation from pressurized packs or nebulizers. The compositions may also be delivered as powders, which may be formulated and the powder composition may be inhaled with the aid of an insufflation powder inhaler device. The preferred delivery systems for inhalation are metered dose inhalation (MDI) aerosol, which may be formulated as a suspension or solution of the instant composition in suitable propellants, such as fluorocarbons or hydrocarbons and dry powder inhalation (DPI) aerosol, which may be formulated as a dry powder of the composition with or without additional excipients.

Suitable topical formulations of the compositions of the present invention include transdermal devices, aerosols, creams, solutions, ointments, gels, lotions, dusting powders, and the like. The topical pharmaceutical compositions containing the compositions of the present invention ordinarily include about 0.005% to 5% by weight of the active compounds in admixture with a pharmaceutically acceptable vehicle. Transdermal skin patches useful for administering the compositions of the present invention include those well known to those of ordinary skill in that art. To be administered in the form of a transdermal delivery system, the dosage administration will be continuous rather than intermittent throughout the dosage regimen.

The compositions of the present invention can also be administered in the form of liposome delivery systems, such as small unilamellar vesicles, large unilamellar vesicles and multilamellar vesicles. Liposomes can be formed from a variety of phospholipids, such as cholesterol, sterylamine or phosphatidylcholines.

Compositions of the present invention may also be delivered by the use of monoclonal antibodies as individual carriers to which the compound molecules are coupled. The compounds in these compositions may also be coupled with soluble polymers as targetable drug carriers. Such polymers can include polyvinylpyrrolidone, pyran copolymer, polyhydroxypropyl-methacrylamide phenol, polyhydroxyethylasparamidepheon, or polyethyleneoxidepolylysine substituted with palmitoyl residues.

Furthermore, the compositions of the present invention may be coupled to a class of biodegradable polymers useful in achieving controlled release of a drug, for example, polylactic acid, polyepsilon caprolactone, polyhydroxybutyric acid, polyorthoesters, polyacetals, polydihydropyrans, polycyanoacrylates and cross-linked or amphipathic block copolymers of hydrogels.

Compositions of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

Each compound in the compositions of the present invention (e.g. selective NPY5R antagonist, co-therapeutic agent) can be combined as the active ingredients in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules, pellet, powder and tablets, with the solid oral preparations being preferred over the liquid preparations. Because of their ease of administration, tablets and capsules represent the typical oral dosage unit form, in which case solid pharmaceutical carriers are employed. If desired, tablets may be coated by standard aqueous or non-aqueous techniques.

In addition to the common dosage forms set out above, the composition may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredients, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients.

Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

For example, for oral administration in the form of a tablet, capsule, pellet, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs, syrups, slurries, emulsions, suspensions, solutions, and effervescent compositions, the oral drug components can be combined with any oral, non-toxic, pharmaceutically acceptable inert carrier such as ethanol, glycerol, water, oils and the like. Moreover, when desired or necessary, suitable binders, lubricants, disintegrating agents, buffers, coatings, and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. When a dosage unit form is a capsule, it may contain, in addition to materials of the above type, a liquid carrier such as a fatty oil.

Desirably, each tablet contains from 0.01 to 1,000 mg, particularly 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of the active ingredient; and each cachet or capsule contains from about 0.01 to 1,000 mg, particularly 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of the active ingredient.

EXEMPLIFICATION

Materials and Methods siRNAs and reagents: NPY5R siRNA pool and siRNA control were purchased from Dharmacon, Colo., USA. Transfection reagent Lipofectamine 2000 was purchased from Invitrogen Canada, Burlington, ON, Canada. The reagents for the SRB assay were from Sigma Canada, Oakville, ON, Canada.

Transfection of siRNAs into cancer cell lines: 8 different cancer cell lines were used for the siRNA transfection, including CAMA-1, Hs578T, MCF-7, MDA-MB-231, MDA-MB-435, MDA-MB-468, SKBR-3, and T47D. Cells were seeded at various concentrations, ranging from 1500 to 6000 per well according to cell growth rate, into 96-well plates. 40 nM siRNAs pool, which contains 4 individual siRNAs at 10 nM each, were transfected into cells using Lipofectamine2000 24 hours after cell seeding. The RNA sequences of 4 siRNAs used in the pool are:

```
                                         (SEQ ID NO: 1)
NPY5R (1):    5'-UAACACACAUGCUGUCUUCUU-3';

(SEQ ID NO: 2)
NPY5R (2):    5'-UAAUAUGGCACAUGACUUUUU-3';

(SEQ ID NO: 3)
NPY5R (3):    5'-UUACUCUCAAUUCAUGAACUU-3';

(SEQ ID NO: 4)
NPY5R (4):    5'-AACACUUCGAGAUCUCUUUUU-3'.
```

Non-targeting siRNA pool (siPOOL) was transfected into cells as positive control and siCONTROL TOX™ transfection control (siTOX) was used as transfection efficiency control. Cells were then incubated at 37° C. for five days before cell viability assay were conducted.

Sulforhodamine B (SRB) assay: SRB assay was performed to assess cell survival. The cells were fixed in situ by gently aspirating off the culture media and adding 50 ul ice cold 10% Tri-chloroacetic Acid (TCA) per well and incubated at 4° C. for 30-60 minutes. The plates were washed with tap water five times and allowed to air dry for 5 minutes. 50 ul 0.4% (w/v) Sulforhodamine B solution in 1% (v/v) acetic acid per well was added and incubated for 30 minutes at room temperature for staining. Following staining, plates were washed four times with 1% acetic acid to remove any unbound dye and then allowed to air dry for 5 minutes. Stain was solubilized with 100 ul of 10 mM Tris pH10.5 per well. Absorbance was read at 570 nm.

Data analysis: SRB is a water-soluble dye that binds to the basic amino acids of the cellular proteins. Thus, colorimetric measurement of the bound dye provides an estimate of the total protein mass that is related to the cell number. The cell survival percentage after each siRNA(s) knocking down was calculated over the non-silencing control siPOOL as well as siTOX for transfection efficiency control.

EXAMPLE 1 siRNA Knockdown of NPY Y5 Receptor

TABLE 1

| | | | | | | | | | | |
|---|---|---|---|---|---|---|---|---|---|---|
| Depletion of NPY5R Expression | | | | | | | | | | |
| NPY5R siRNA | SKBR-3 | MDA-M-435 | MDA-MB-231 | T47D | MDA-MB-468 | CAMA-1 | Hs578T | 184A | HMEC-C | MCF-7 |
| siRNA1 | 0.60 | 0.66 | 0.46 | 1.08 | 0.96 | 1.12 | 0.88 | 1.12 | 1.17 | 0.62 |
| siRNA2 | 0.86 | 0.43 | 0.64 | 0.82 | 0.53 | 0.89 | 0.46 | 0.83 | 0.89 | 0.46 |

TABLE 1-continued

Depletion of NPY5R Expression

| NPY5R siRNA | SKBR-3 | MDA-M-435 | MDA-MB-231 | T47D | MDA-MB-468 | CAMA-1 | Hs578T | 184A | HMEC-C | MCF-7 |
|---|---|---|---|---|---|---|---|---|---|---|
| siRNA3 | 0.60 | 0.49 | 0.84 | 0.52 | 0.59 | 0.32 | 0.50 | 0.28 | 0.66 | 0.56 |
| siRNA4 | 0.77 | 0.41 | 0.79 | 0.87 | 0.62 | 1.23 | 0.75 | 0.78 | 0.97 | 0.78 |

EXAMPLE 2

Cell Cycle Analysis

Breast cancer cell line MDA-MB-468 and lung cancer cell line A549 were purchased from ATCC. Cells were grown in ATCC suggested medium and plated in a 6-well plate ($2\times10^5$ per well) in medium with 5.6 mM glucose one day before siRNA transfection.

NPY5R siRNA pool was mixed from 4 individual duplexes which were purchased from Dharmacon. Lipofectamine-2000 (Invitrogen) was used for siRNA transfection following the Invitrogen siRNA transfection protocol. Final 40 nM siRNA was transfected into cultured cells.

Figure 2:
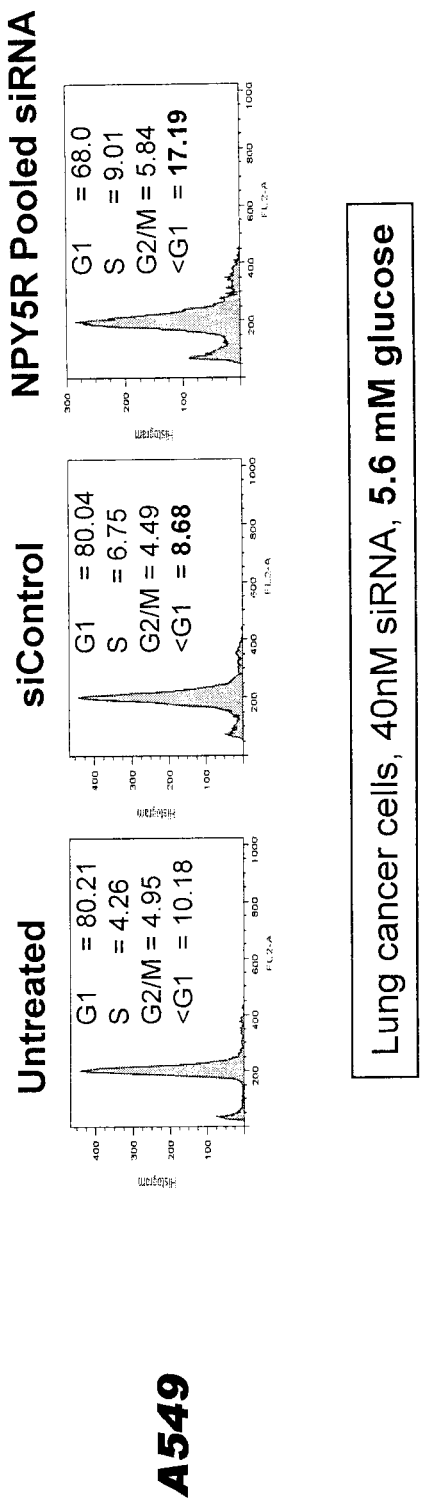
FIG. 2 is a series of fluorescence histograms illustrating the effect of depletion of NPY5R expression on A549 lung cancer cells using siRNA. The graphs show that depletion of NPY5R (NPY5R Pooled siRNA) induces cell death. The increased sub-G1 (<G1) population of cells indicates increased cell death.
Figure 3:
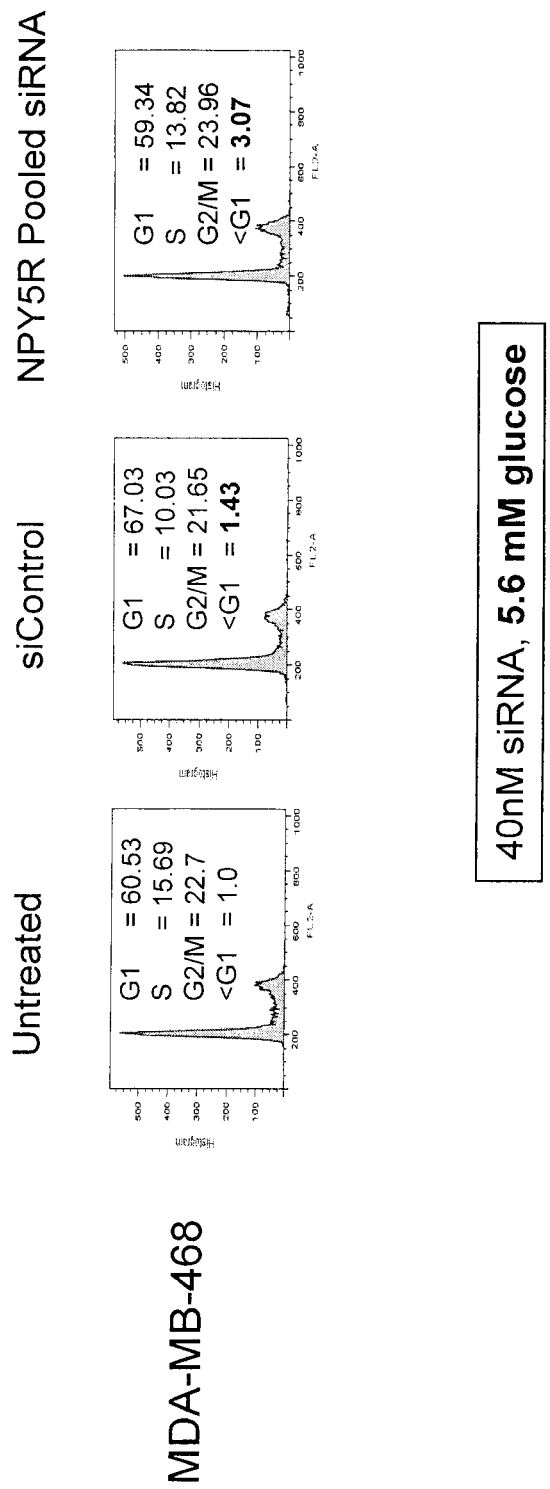
FIG. 3 is a series of graphs illustrating the effect of depletion of NPY5R expression on MDA-MB-468 breast cancer cells. The graphs show that depletion of NPY5R(NPY5R Pooled siRNA) induces cancerous cell death. The increased sub-G1 (<G1) population of cells indicates increased cell death.

Cells were collected 3 days post siRNA transfection, washed by PBS-0.1% BSA once, and fixed by 75% Ethanol-PBS-0.1% BSA at 40 C for at least 1 hour. After washing with PBS-0.1% BSA twice, cells were stained by 50 ug/ml propidium iodide-10 ug/ml RNaseA in PBS for overnight. Cell cycle analysis was done by flow cytometry the next day (FIGS. 2 and 3).

EXAMPLE 3

NPY5R Expression in Multiple Cancer Cell Lines

Figure 4:
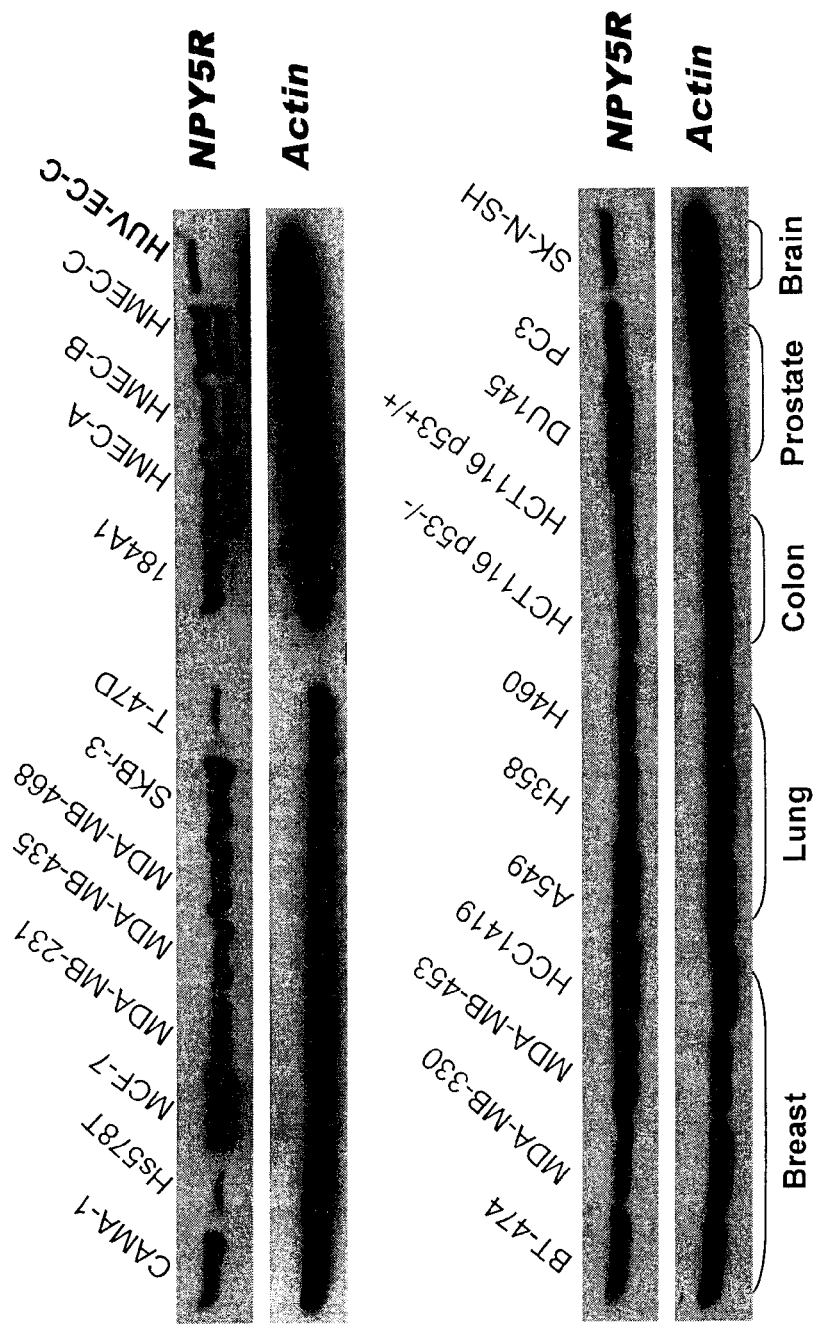
FIG. 4 is a photograph of a western blot illustrating NPY5R expression in multiple breast, lung, colon, prostate and brain cancer cell lines.

The expression of Y5 receptor in cancer cell lines derived from several major cancer types (breast, lung, colon, prostate and brain) was examined by Western Blot (FIG. 4). High levels of NPY5R protein were detected in all of the cancer cell lines examined, consistent with its potential role in a wide range of cancers.

EXAMPLE 4

NPY5R Antagonist MK0557 Treatment

Figure 5:
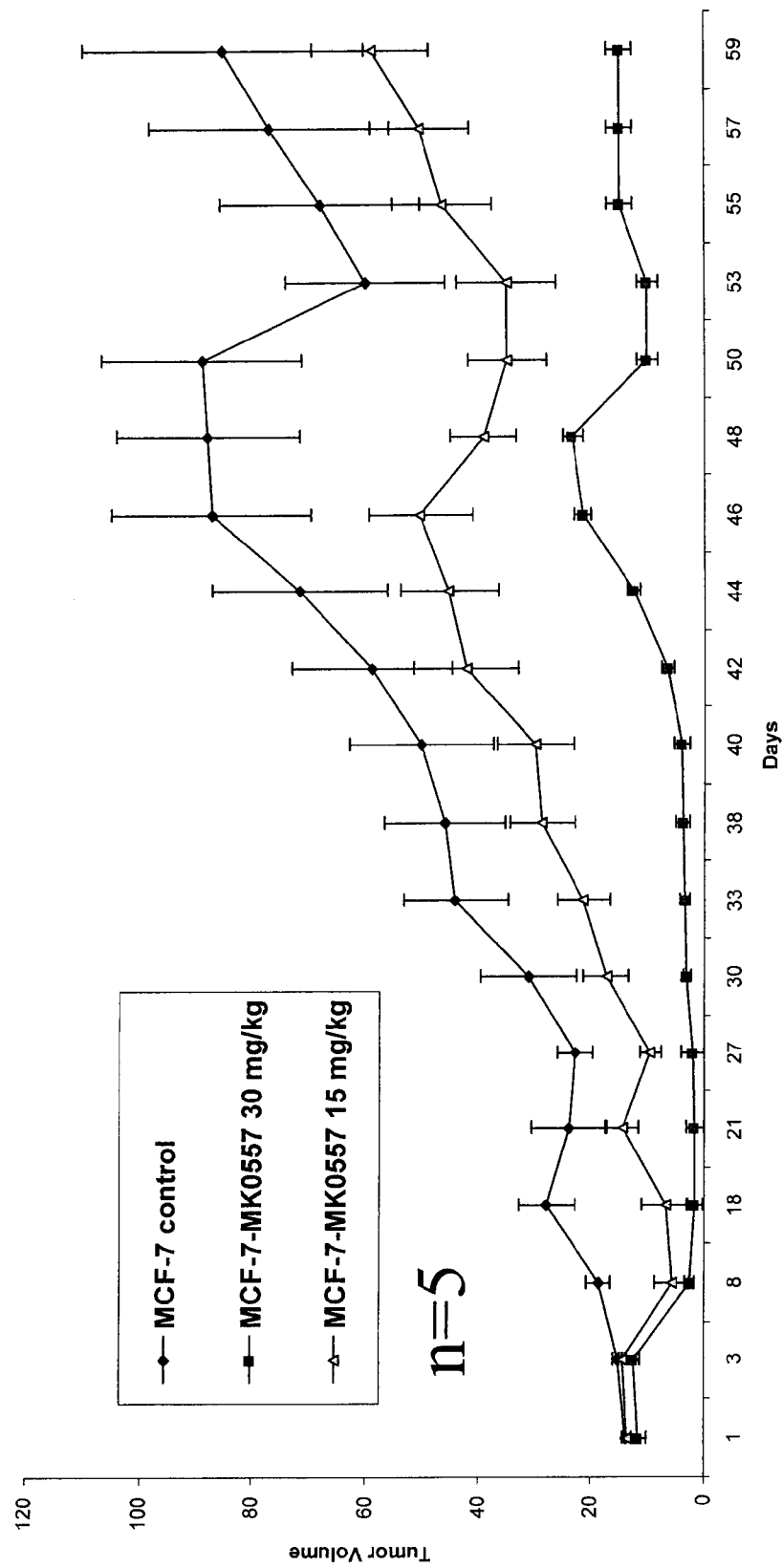
FIG. 5 is a graph illustrating dose-dependent inhibition of tumor growth in a breast cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

MCF-7 cells were dissociated from flask surfaces then counted and spun down with a final concentration of $10\times10^7$ cells/ml produced. A total of 20 SCID mice, aged 6-8 weeks (CRL-CB17), were injected with $10\times10^6$ cells into lower mammary fat pads. After 3 weeks, all mice were inspected for tumor establishment and were measured for size (FIG. 5).

For this study, a total of 15 mice were selected from a group of 20, which had similar tumor sizes (3×3). Subsequently, these 15 mice were divided into three groups of 5. The first group, the control group, received the vehicle only (20% ETOH and 80% PEG 400); the second group received a dosage of 30 mg/kg of MK0557; and the third group received a dosage of 15 mg/kg of MK0557.

All groups were injected everyday via IP for the first five days, followed by injections every other day. In the second week, tumor shrinkage was noticed in treated groups especially in the second group, where 4 out of 5 mice were tumor free in the third week.

EXAMPLE 5

Figure 6:
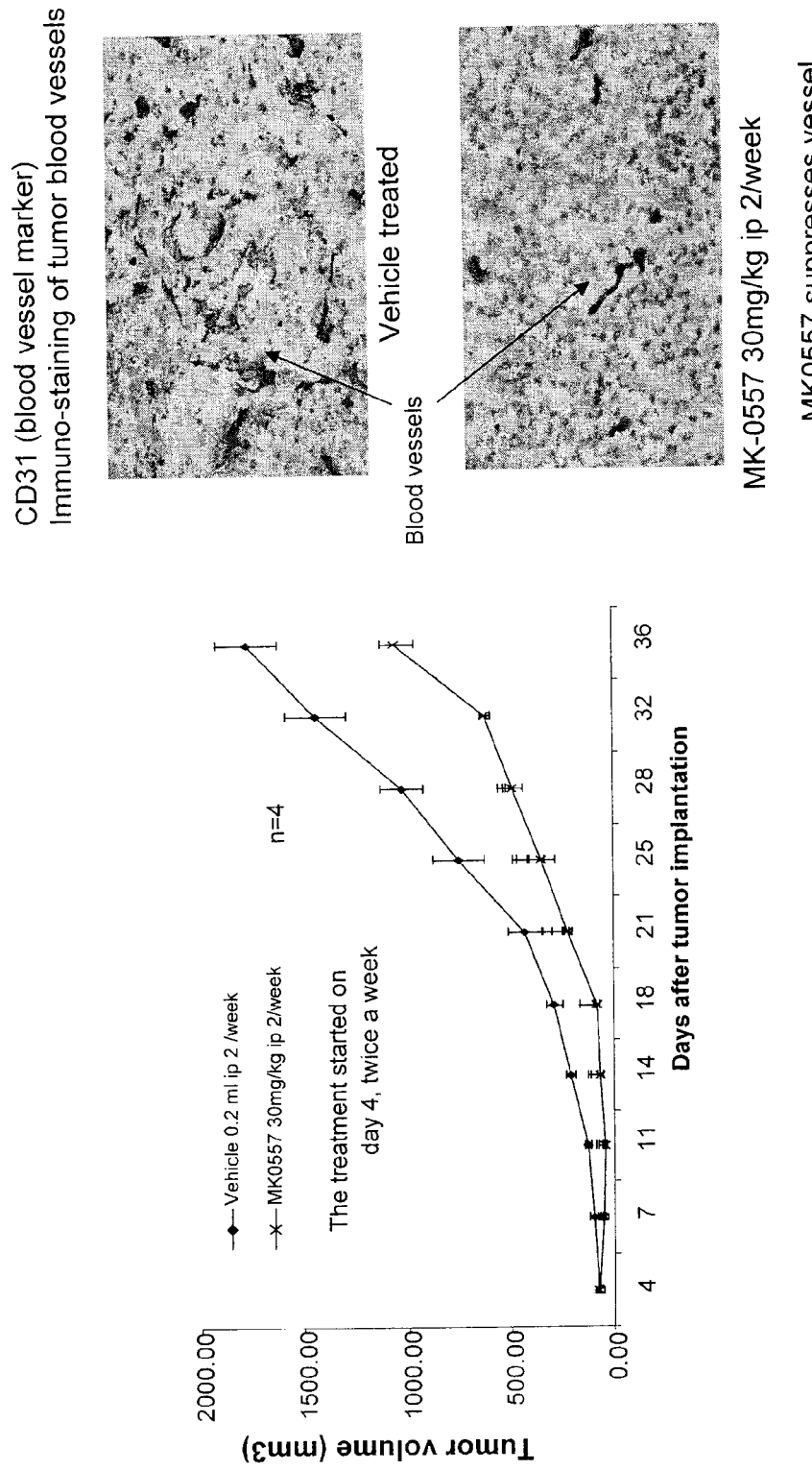
FIG. 6 is a graph illustrating inhibition of tumor growth in a Hodgkin lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

NPY5R Antagonist MK0557 Inhibits Tumor Growth in Hodgkin Lymphoma Xenograft Model Hodgkin Lymphoma cells, HD-MYZ, (4 million) were injected subcutaneously on the left flank of 10-12 week old, female NOD-SCID mice (from The Jackson Lab, Cat#001303). Four days post-implantation, treatments with MK0557 or vehicle were started (Vehicle control: 0.2 ml ip 2/week, MK-0557 30 mg/kg ip 2/week) and lasted for the duration of the experiment. The mice were sacrificed on day 36 when the experiment ended (FIG. 6).

EXAMPLE 6

NPY5R in vitro Angiogenesis Assay

HUV-EC-C cells were purchased from ATCC and routinely cultured in Ham's F12K medium supplemented with 10% FBS, 2 mM L-glutamine, 1.5 g/L sodium bicarbonate, 0.1 mg/ml heparin and 0.03 mg/ml endothelial cell growth supplement (ECGS).

Figure 7:
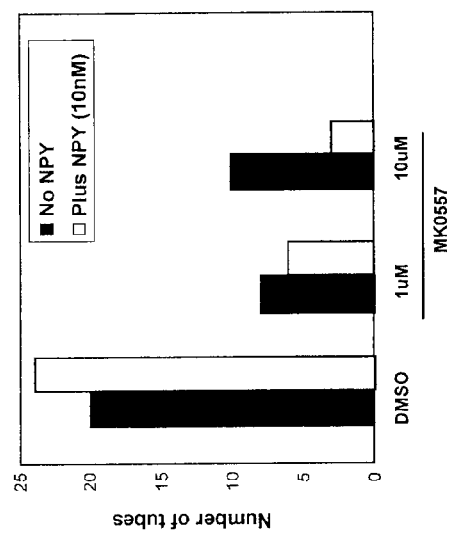
FIG. 7 is a graph illustrating the effect of treatment with selective NPY5R antagonist MK-0557 on tube formation in an in vitro angiogenesis assay. The graph show that treatment with selective NPY5R antagonist MK-0557 inhibits tube formation.

An In Vitro Angiogenesis Assay kit from Chemicon (Cat#ECL625) was used for testing HUV-EC-C tube formation. Cells were incubated on ECMatrix coated 96-well plate at $8\times10^3$ cells per well in growth medium with or without NPY, its antagonist MK0557, or DMSO as a control. Inhibition of in vitro endothelial tubule formation by MK0557 was quantitated from photographs after 5 hours by counting the number of tubes in the well (FIG. 7).

EXAMPLE 7

NPY5R Antagonist MK0557 Inhibits Tumor Growth in Brain Cancer Xenograft Model

Figure 8:
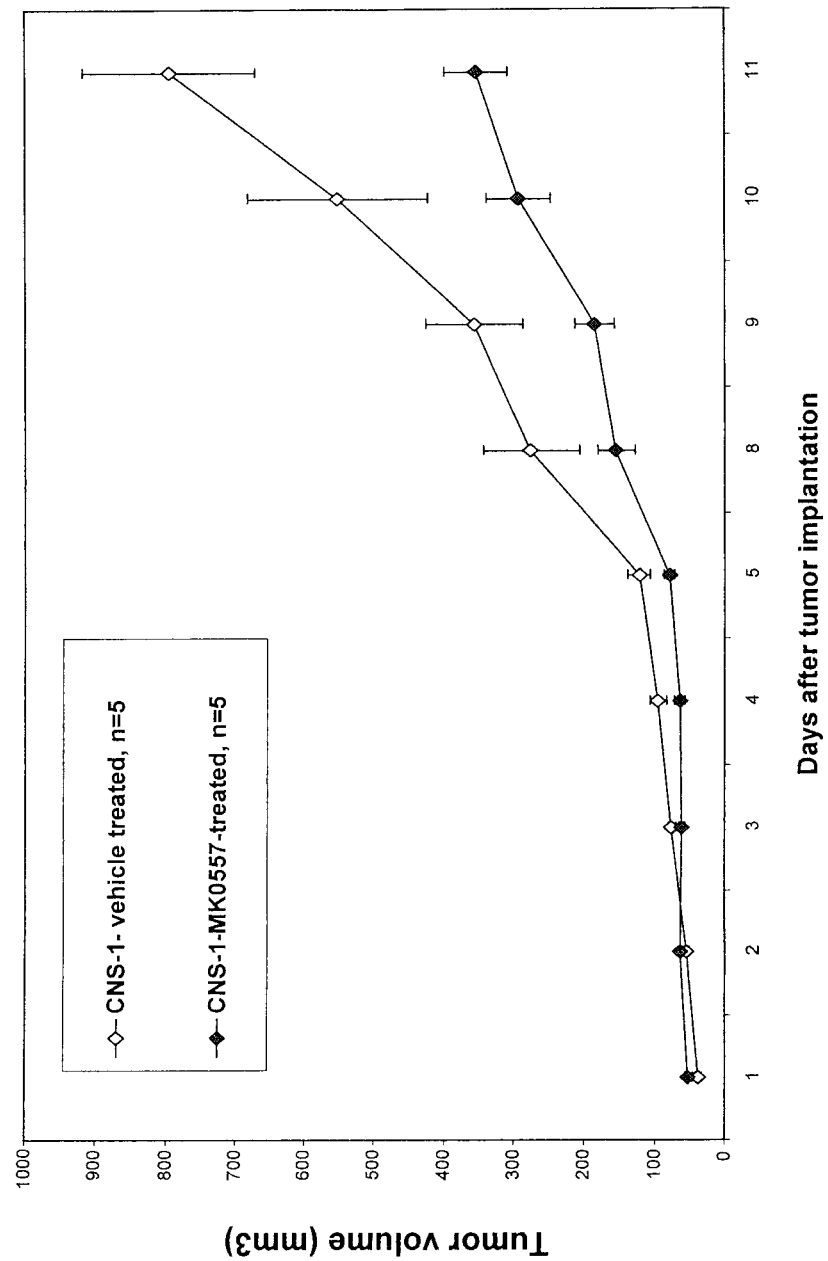
FIG. 8 is a graph illustrating inhibition of tumor growth in a brain cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

Rat glioma cells ($2\times10^6$) were implanted in CB17-SCID mice. The mice were treated with MK0557 at 30 mg/kg, or vehicle (15% of 0.5%) CMC (carboxymethylcelulose) (low viscosity) and 85% of 0.2% Tween80 in water) intraperitoneally daily for the first week followed by once every two days injections. Tumor growth was inhibited, however no obvious effect on mouse body weights were seen (FIG. 8).

EXAMPLE 8

NPY5R Antagonist MK0557 Inhibits Tumor Growth in Colon Cancer Xenograft Model

Figure 9:
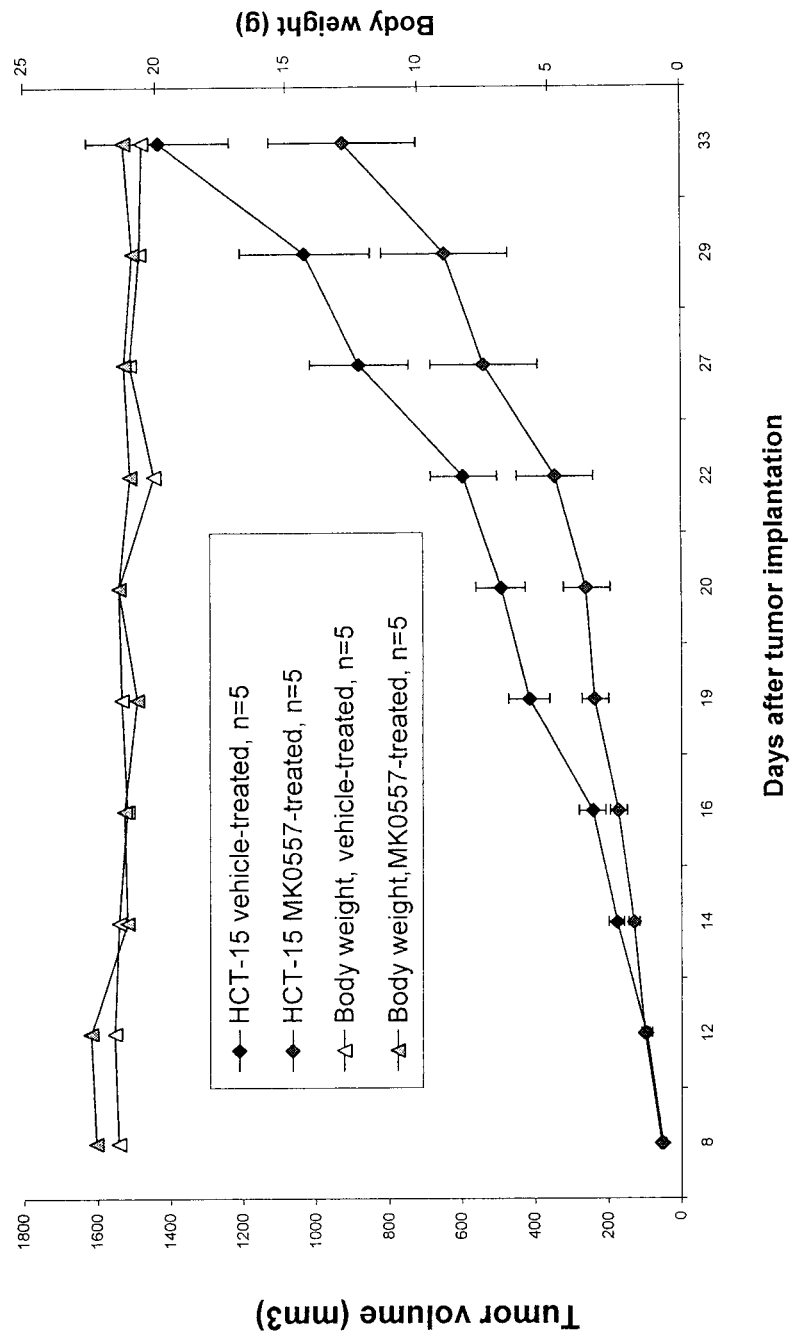
FIG. 9 is a graph illustrating inhibition of tumor growth in a colon cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

Colon cancer cells, HCT-15, ($1\times10^6$) were implanted in CB17-SCID mice. The mice were treated with MK0557 at 30 mg/kg or vehicle (15% of 0.5%) CMC (carboxymethylcelulose) (low viscosity) and 85% of 0.2% Tween80 in water) intraperitoneally daily for the first week followed by once every two days injections. Tumor growth was inhibited, however no obvious effect on mouse body weights were seen (FIG. 9).

EXAMPLE 9

NPY5R Antagonist MK0557 Inhibits Tumor Growth in Lung Cancer Xenograft Model

Figure 10:
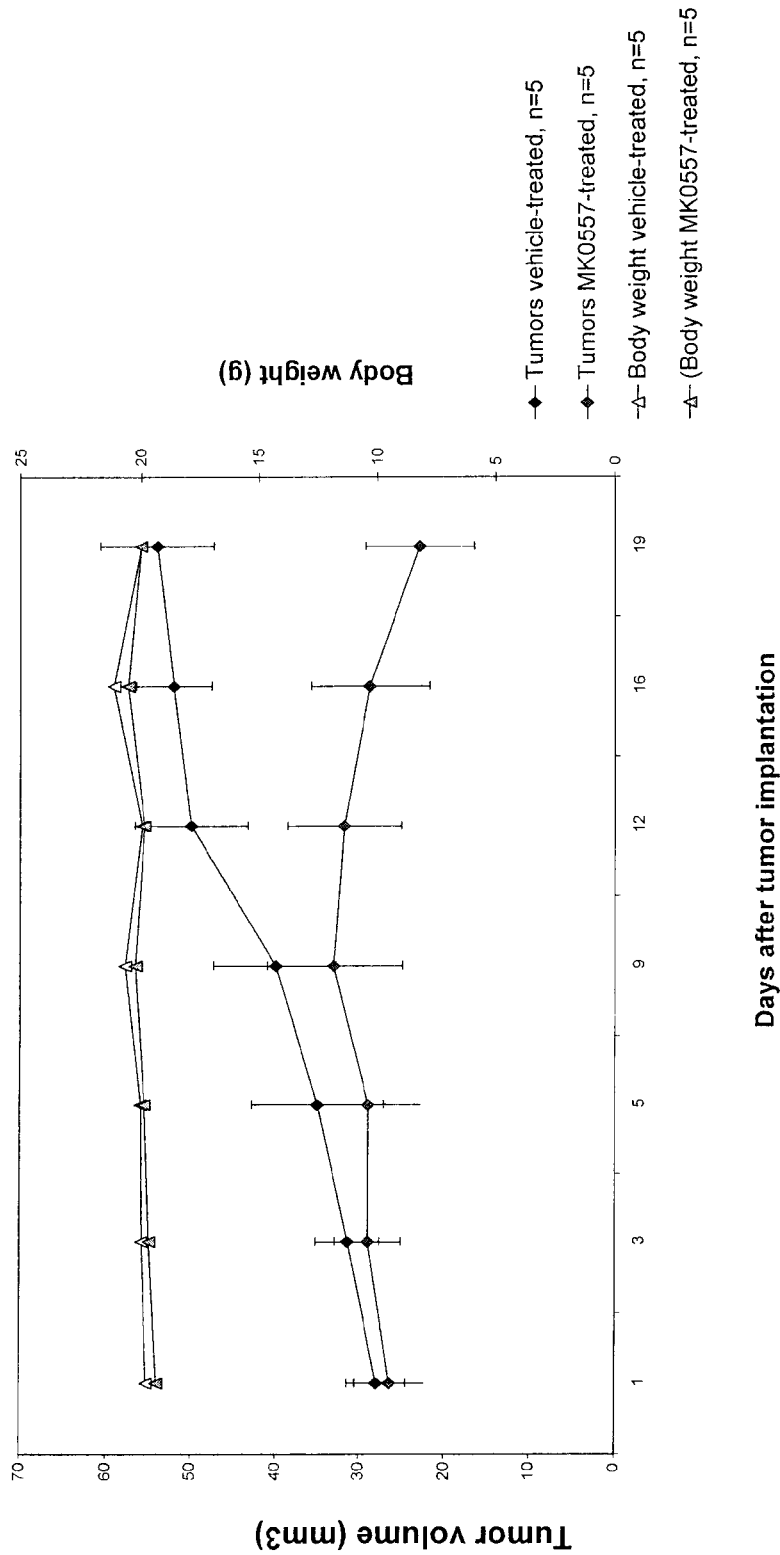
FIG. 10 is a graph illustrating inhibition of tumor growth in a lung cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

Lung cancer cells, H358, (1×10$^6$) were implanted in CB17-SCID mice. Ten days post-implantation, the mice were treated with MK0557 at 30 mg/kg or vehicle (15% of 0.5%) CMC (carboxymethylcelulose) (low viscosity) and 85% of 0.2% Tween80 in water) intraperitoneally daily for the first week followed by once every two days injections. Tumor growth was inhibited, however no obvious effect on mouse body weights were seen (FIG. 10).

EXAMPLE 10

NPY5R Antagonist MK0557 Inhibits Tumor Growth in Ovarian Cancer Xenograft Model

Figure 11:
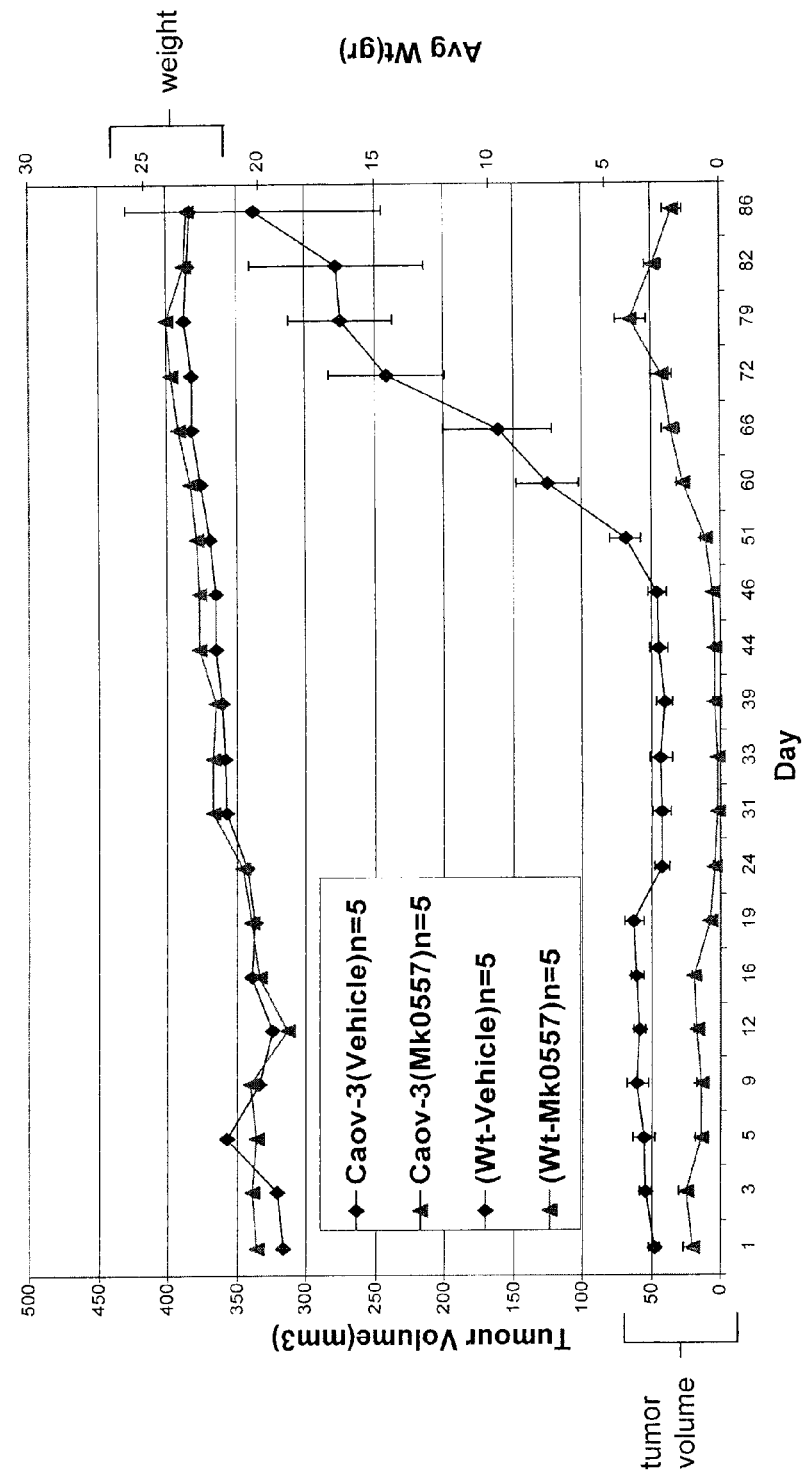
FIG. 11 is a graph illustrating inhibition of tumor growth in an ovarian cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide). Change in body weight was not significantly affected by the NPY5R antagonist.

Ovarian cancer cells, Caov-3 (2 Million), were implanted in CB17-SCID mice. The mice were treated with MK0557 at 30 mg/kg or vehicle (15% of 0.5% of CMC (carboxymethylcellulose, low viscosity) and 85% of 0.2% Tween 80 in water) intraperitoneally daily for the first week followed by once every two days injections. Both the tumor growth and body weights were monitored for the duration of the experiment. (FIG. 11) MK0557 (trans-N-[1-(2-fluorophenyl)-3-pyrazolyl]-3-oxospiro[6 azaisobenzofuran-1(3H), 1'-cyclohexane]-4'carboxamide) inhibited tumor growth. Change in body weight was not significantly affected by the NPY5R antagonist.

EXAMPLE 11

NPY5R Antagonist MK0557 Inhibits Tumor Growth in Breast Cancer Xenograft Model

Figure 12:
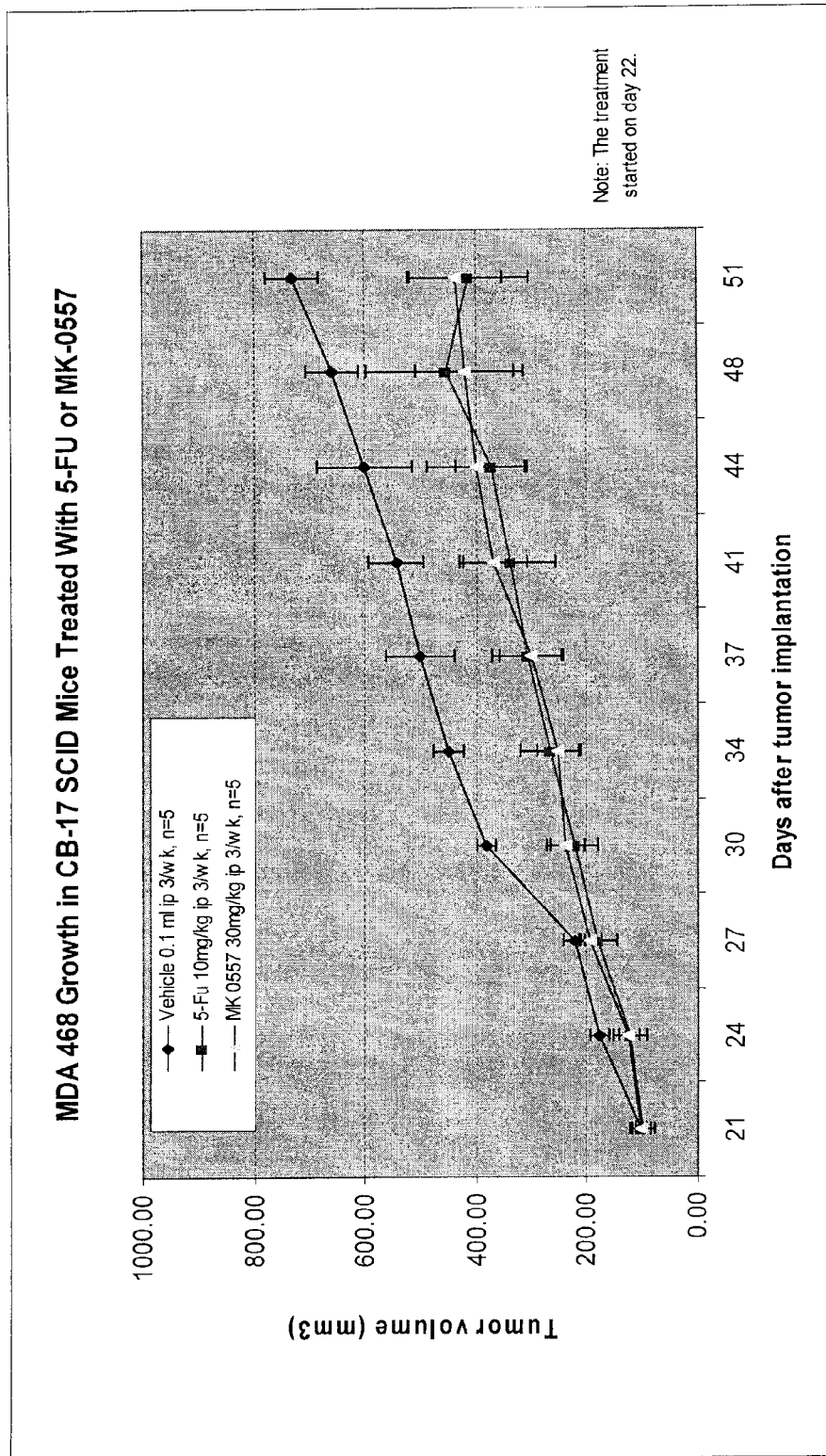
FIG. 12 is a graph illustrating inhibition of tumor growth in a breast cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

Breast cancer cells, MDA MB 468 (12 million), were injected subcutaneously (s.c.) on the neck of SCID mice (CB17, female, 4-6 weeks old) (Charles River, Wilmington, Mass.). The mice were divided into four groups, 5 mice for each group. The treatments were started when the tumor volume reached about 100 mm$^3$, day 22 after tumor implantation. Vehicle control (0.1 ml of 0.1% CMC+0.08% Tween-80 i.p. for 20 g body weight, ip 3/week), 5-FU (10 mg/kg i.p. 3/week) or MK-0557 (30 mg/kg i.p. 3/week) were given for duration of approximately 4 weeks. The tumor sizes were monitored every 3 or 4 days. MK=0557 and 5-FU both inhibited tumor growth. (FIG. 12)

EXAMPLE 12

Figure 13:
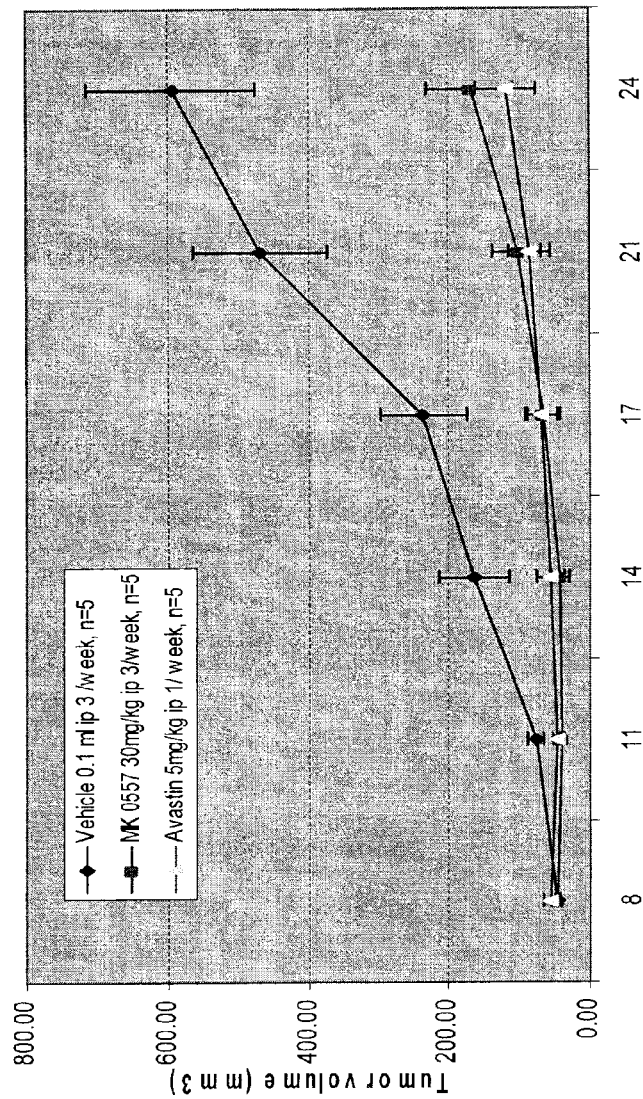
FIG. 13 is a graph illustrating inhibition of tumor growth in a Hodgkin lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

NPY5R Antagonist MK0557 Inhibits Tumor Growth in Hodgkin Lymphoma Xenograft Model Hodgkin lymphoma cells, HD-MYZ (1 million), were implanted s.c. on the right flank of NOD-SCID mice (Cat#001303, female, 4-6 weeks from Jackson laboratories, Bar Harbor, Me.). The mice were divided into four groups, 5 mice for each group. The treatments were started when the tumor volume reached about 50 mm$^3$, day 8 after tumor implantation: The mice were treated with vehicle control (0.1 ml of 0.1% CMC+0.08% Tween-80 i.p. for 20 g body weight, 3/week), MK-0557 (30 mg/kg i.p. 3/week) or AVASTIN® (bevacizumab, Genentech; 5 mg/kg i.p. 1/week) for approximately 2 weeks. The tumor growth was monitored during the experiment. MK-0557 and AVASTIN® (bevacizumab, Genentech) both inhibited tumor growth. (FIG. 13)

EXAMPLE 13

NPY5R Antagonist MK0557 Inhibits Tumor Growth in Ovarian Cancer Xenograft Model

Figure 14:
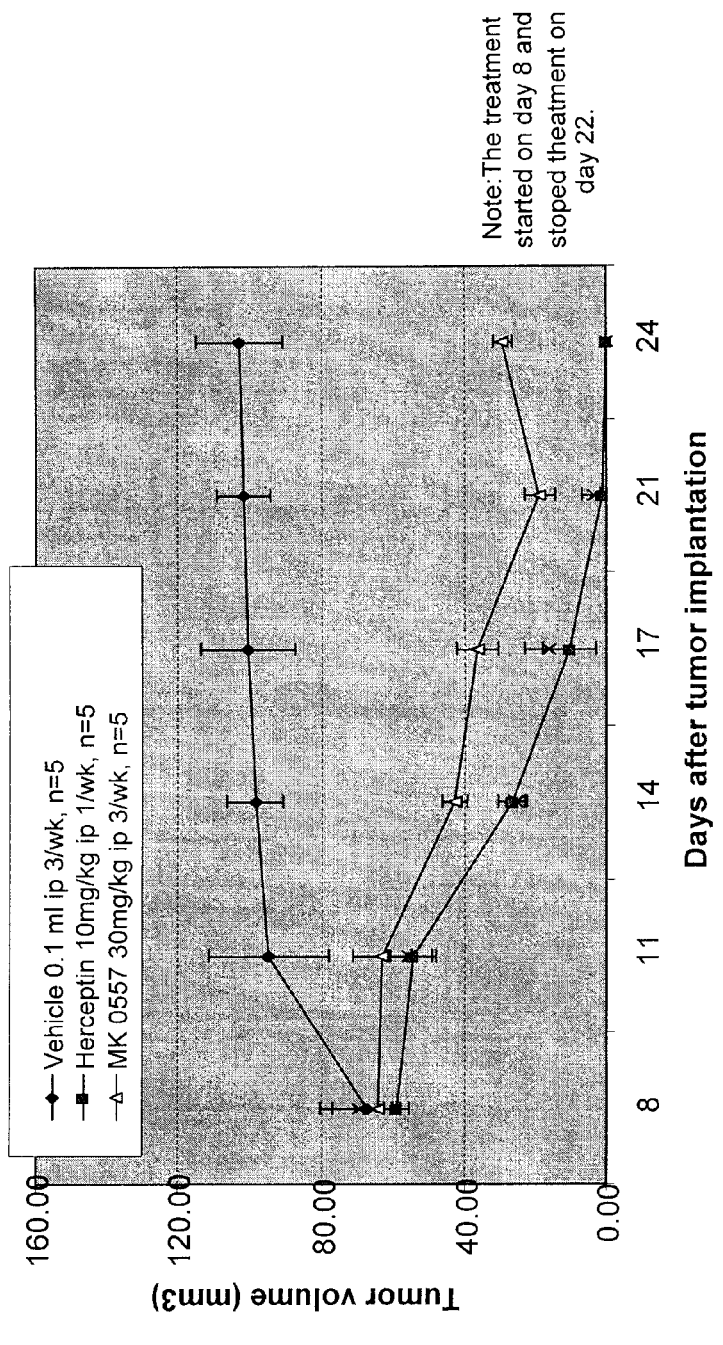
FIG. 14 is a graph illustrating inhibition of tumor growth in an ovarian cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide).

Ovarian cancer cells SKOV-3 (5 millions) were implanted s.c. on the right flank of SCID mice (CB17, female, 4-6 weeks) (Charles River, Wilmington, Mass.). The mice were divided into four groups, 5 mice for each group. The treatments were started when the tumor volume reached at around 60 mm3, day 8 after tumor implantation. The mice were treated with vehicle control (0.1 ml of 0.1% CMC+0.08% Tween-80 i.p. for 20 g body weight, 3/week), HERCEPTIN® (trastuzumab, Genentech; 10 mg/kg i.p. 1/week) Or MK-0557 (30 mg/kg i.p. 3/week). The tumor growth was monitored for the duration of the experiment. MK-0557 and HERCEPTIN® (trastuzumab, Genentech) both inhibited tumor growth. (FIG. 14)

EXAMPLE 14

NPY5R Antagonist MK0557 Inhibits Tumor Growth in Hodgkin Lymphoma Xenograft Model (MK0557 vs AVASTIN®)

Figure 15:
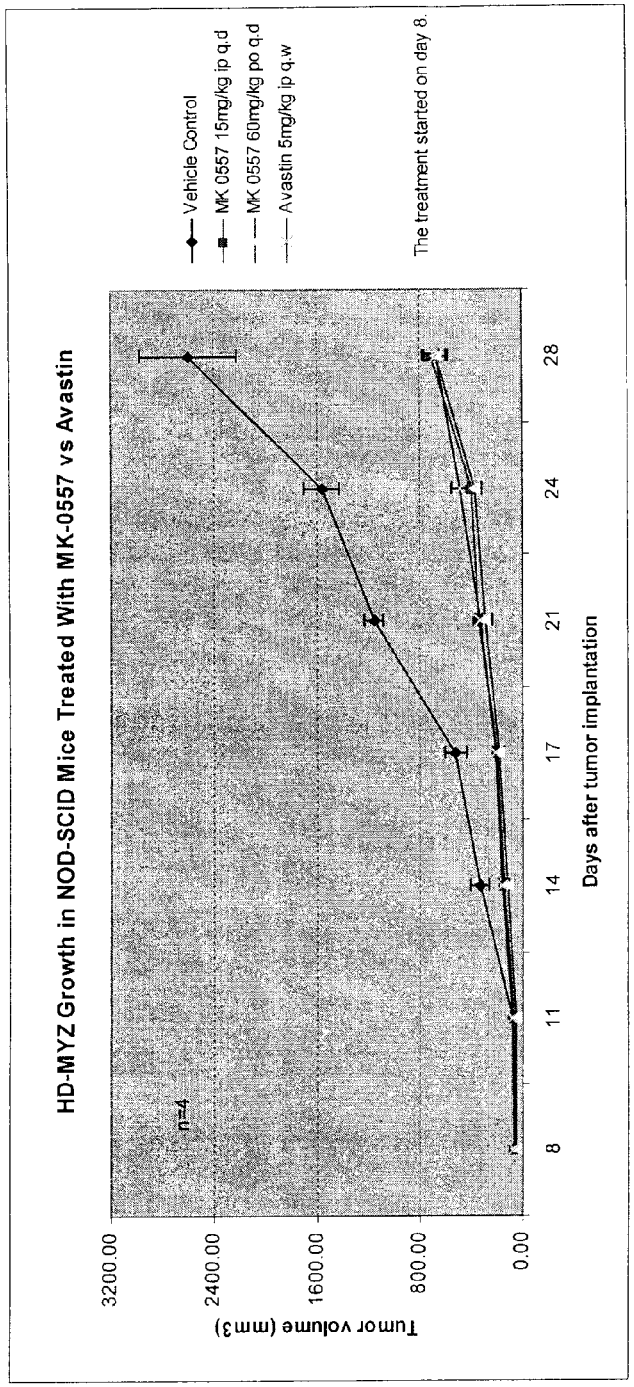
FIG. 15 is a graph illustrating inhibition of tumor volume in a Hodgkin lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide) or AVASTIN®.
Figure 16:
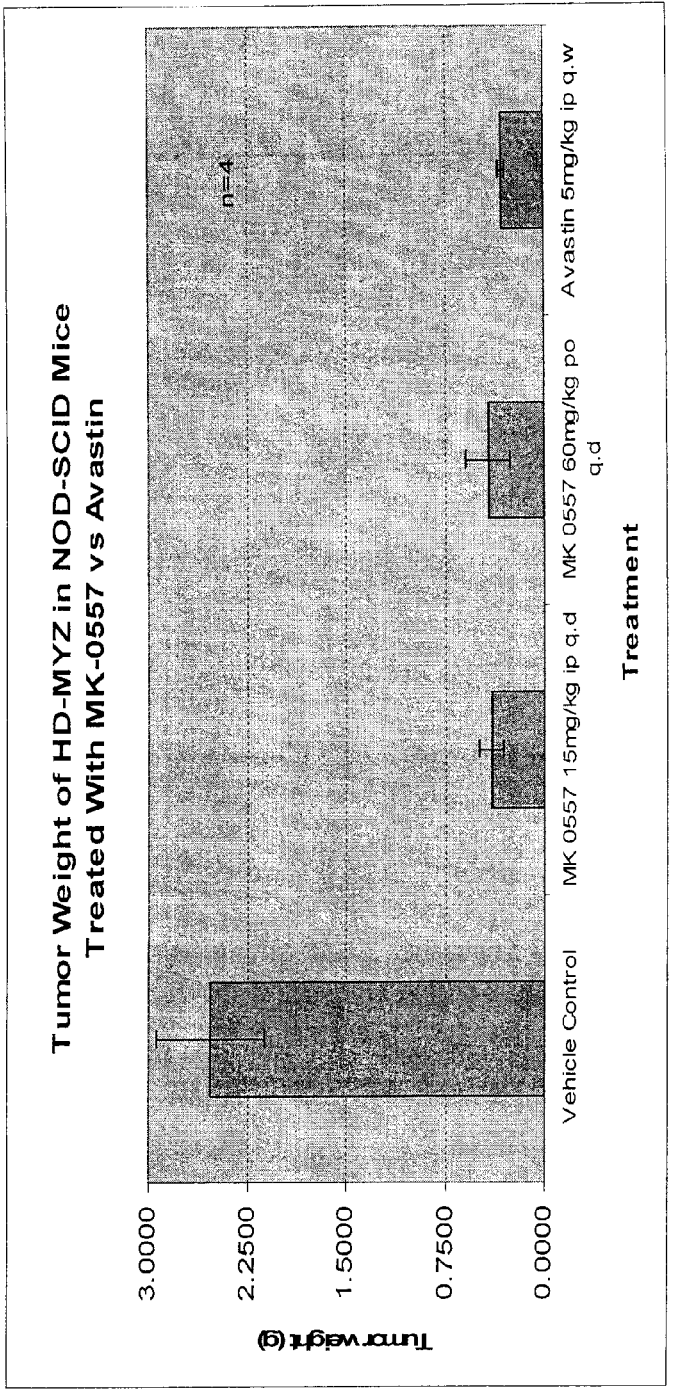
FIG. 16 is a bar graph illustrating inhibition of tumor weight in a Hodgkin lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide) or AVASTIN®.

Hodgkin lymphoma cells, HD-MYZ, were implanted in NOD-SCID mice. The treatments were started day 8 after tumor implantation: The mice were treated with vehicle control, MK-0557 (15 mg/kg intraperitoneal (ip), every day (q.d.)), MK-0557 (60 mg/kg, by mouth (po) q.d.) or AVASTIN® (bevacizumab, Genentech; 5 mg/kg ip q.w.) for approximately 3 weeks. Tumor volume and tumor growth were monitored during the experiment.
Comparing Mean Tumor Volume (mm$^3$)
In MK-0557 15 mg/kg i.p. every day×3 weeks treated mice was 698.76±61.19 versus 2600.76±383.72 in vehicle group mice; inhibition rate: 73.13%. In MK-0557 60 mg/kg p.o. every day×3 weeks treated mice was 671.97±96.89 versus 2600.76±383.72 in vehicle group mice; inhibition rate: 74.16%. In AVASTIN® 5 mg/kg i.p. 1/week×3 weeks treated mice was 672.53±85.56 versus 2600.76±383.72 in vehicle group mice; inhibition rate: 74.14%. See FIG. 15.
Comparing Mean Tumor Weight (g)
In MK-0557 15 mg/kg i.p. every day×3 weeks treated mice was 0.40±0.09 versus 2.53±0.41 in vehicle group mice; inhibition rate: 84.19%. In MK-0557 60 mg/kg p.o. every day×3 weeks treated mice was 0.43±0.17 versus 2.53±0.41 in vehicle group mice; inhibition rate: 83.0%. In AVASTIN® 5 mg/kg i.p. 1/week×3 weeks treated mice was 0.33±0.03 versus 2.53±0.41 in vehicle group mice; inhibition rate: 86.96%. See FIG. 16.

EXAMPLE 15

NPY5R Antagonist MK0557 and 5-FU Inhibits Tumor Growth in Breast Cancer Xenograft Model Breast cancer cells, MDA MB 468, were injected into CB17-SCID. The treatments were started day 14 after tumor implantation. Vehicle control (0.1 ml ip q.d.×5 days+Vehicle 2 0.1 ml, ip 3/week), 5-FU (30 mg/kg ip q.d.×5 days) or MK-0557 (30 mg/kg ip. 3/week) and 5-FU (30 mg/kg ip q.d.×5 days)+MK-0557 (30 mg/kg ip. 3/week). Tumor volume and tumor growth were monitored during the experiment.

Comparing Mean Tumor Volume ($mm^3$)

Figure 17:
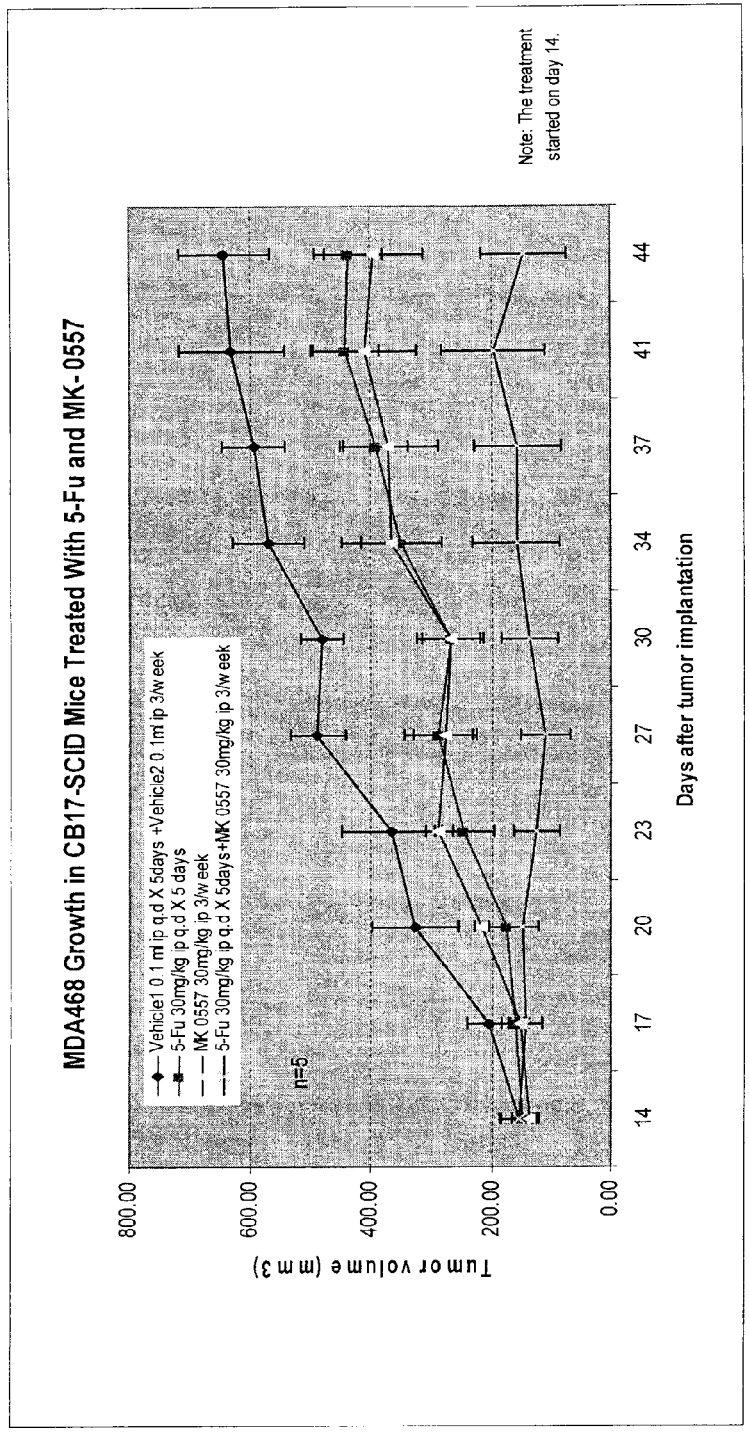
FIG. 17 is a graph illustrating inhibition of tumor volume in a breast cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 5-FU and MK0557 in combination with 5-FU.

In 5-FU alone treated mice was 434.44±56.63 versus 642.20±75.47 in vehicle group mice; inhibition rate: 32.35%. In MK0557 alone treated mice was 392.73±80.63 versus 642.20±75.47 in vehicle group mice; inhibition rate: 38.85%. In 5-FU+MK0557 treated mice was 144.27±70.61 versus 642.20±75.47 in vehicle group mice; inhibition rate: 77.54%. See FIG. 17.

Comparing Mean Tumor Weight (g)

Figure 18:
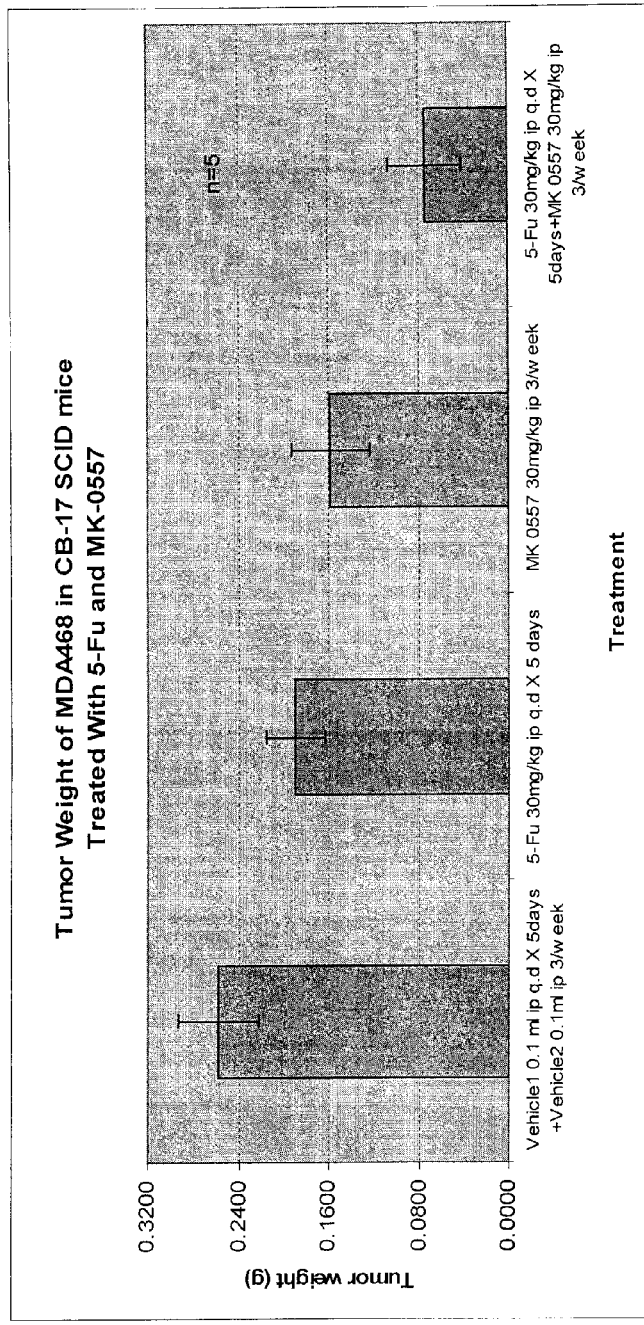
FIG. 18 is a bar graph illustrating inhibition of tumor weight in a breast cancer xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 5-FU and MK0557 in combination with 5-FU.

In 5-FU alone treated mice was 0.1892±0.026 versus 0.2576±0.0358 in vehicle group mice; inhibition rate: 26.55%. In MK0557 alone treated mice was 0.1582±0.0345 versus 0.2576±0.0358 in vehicle group mice; inhibition rate: 38.59%. In 5-FU+MK0557 treated mice was 0.0738±0.0328 versus 0.2576±0.0358 in vehicle group mice; inhibition rate: 71.35%. See FIG. 18.

EXAMPLE 16

NPY5R Antagonist MK-0557 and 200464 Inhibits Tumor Growth in Hodgkin's Lymphoma Xenograft Model Hodgkin lymphoma cells, HD-MYZ, were implanted in NOD-SCID mice, female, 4-6 weeks from Jackson's Laboratory (Maine). The treatments were started day 6 after tumor implantation. The mice were divided to six groups, 4-5 mice from each group. The treatment started with a tumor volume of about 70 mm3 after tumor implantation. The six treatment groups were as follows: 1) vehicle control: 0.1 ml of 0.1% CMC+0.08% Tween-80 for 20 g body weight i.p. 3 times for each week; 2) 200464 20 mg/kg in vehicle i.p. 3 times for each week; 3) 200464 40 mg/kg in vehicle i.p. 3 times for each week; 4) MK 0557 30 gm/kg in vehicle i.p. 3 times for each week; 5) 200464 20 mg/kg in vehicle i.p. 3 times for each week and MK 0557 30 mg/kg in vehicle i.p. 3 times for each week; and 6) 200464 40 mg/kg in vehicle i.p. 3 times for each week and MK 0557 30 mg/kg in vehicle i.p. 3 times for each week (200464 decreased to 20 mg/kg after day 12 due to toxicity).

Results

Comparing Mean Tumor Volume ($mm^3$)

Figure 19:
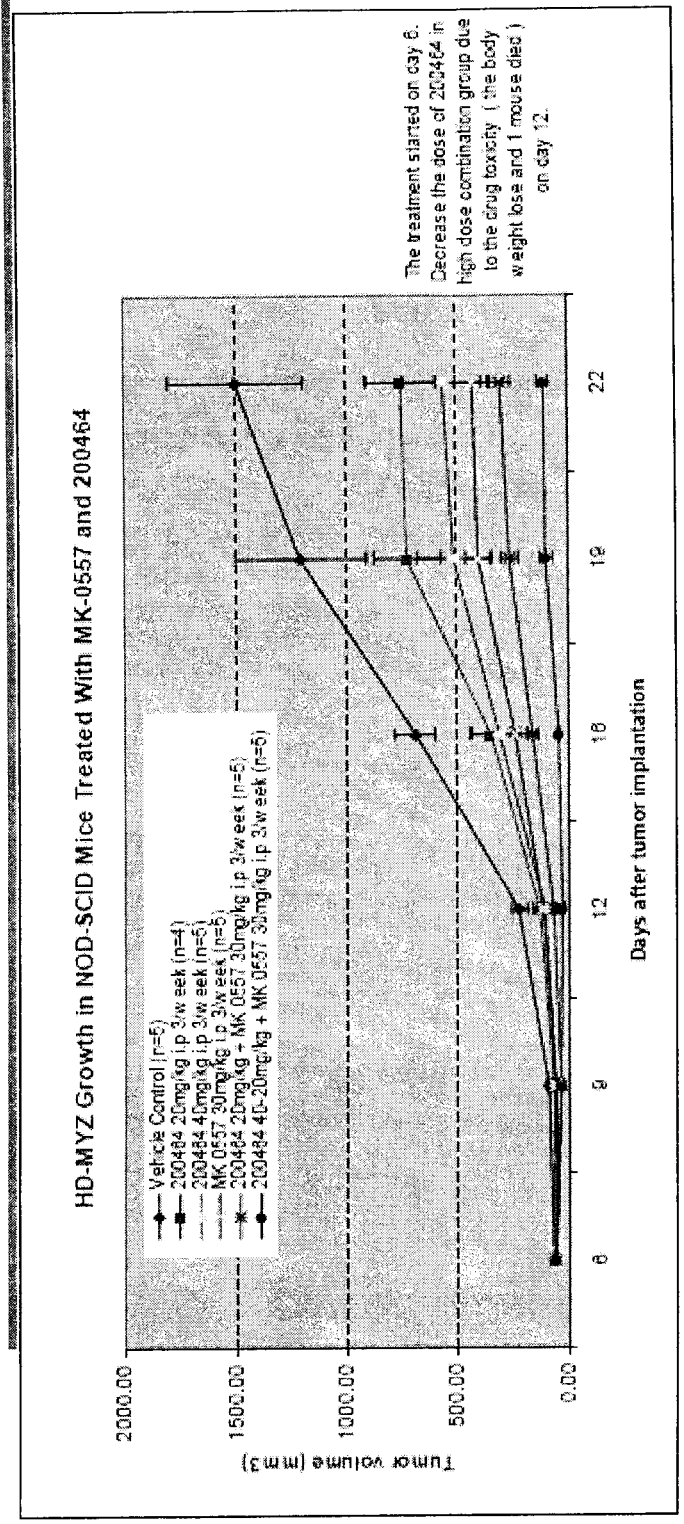
FIG. 19 is a graph illustrating inhibition of tumor volume in a Hodgkin's Lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536).

The inhibitor effect of MK0557 and 200464 on tumor volume in the xenograft model of Hodgkin's Lymphoma is shown in FIG. 19. In group 6, the dose of 200464 was reduced due to drug toxicity (e.g., one mouse died and there was a reduction in body weight). In group 2, the mean tumor volume was 754.55+/−158.32 $mm^3$ versus 1498.94+/−305.12 $mm^3$ for vehicle with an inhibition rate of 62.26% and p-value of 0.21. In Group 3 the mean tumor volume was 565.75+/−176.13 $mm^3$ versus 1498.94+/−305.12 $mm^3$ for vehicle with an inhibition rate of 49.66% and p-value of 0.35. In Group 4 the mean tumor volume was 435.54+/−72.17 $mm^3$ versus 1498.94+/−305.12 $mm^3$ for vehicle with an inhibition rate of 70.94% and p-value of 0.14. In Group 5 the mean tumor volume was 306.20+/−48.68 $mm^3$ versus 1498.94+/−305.12 $mm^3$ for vehicle with an inhibition rate of 79.57% and p-value of 0.09. In Group 6 the mean tumor volume was 112.03+/−29.67. $mm^3$ versus 1498.94+/−305.12 $mm^3$ for vehicle with an inhibition rate of 92.53% and p-value of 0.05.

Comparing Mean Tumor Weight (g)

Figure 20:
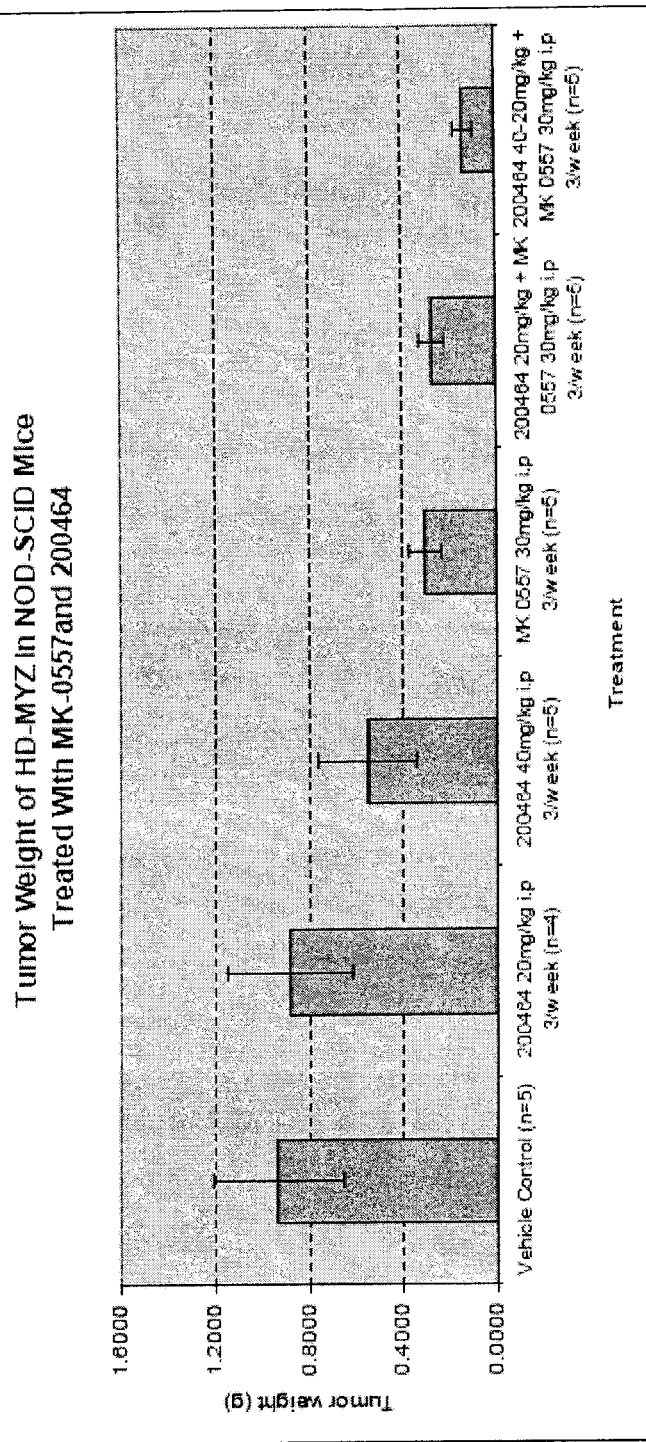
FIG. 20 is a bar graph illustrating inhibition of tumor volume in a Hodgkin's Lymphoma xenograft model using the selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536).
Figure 21:
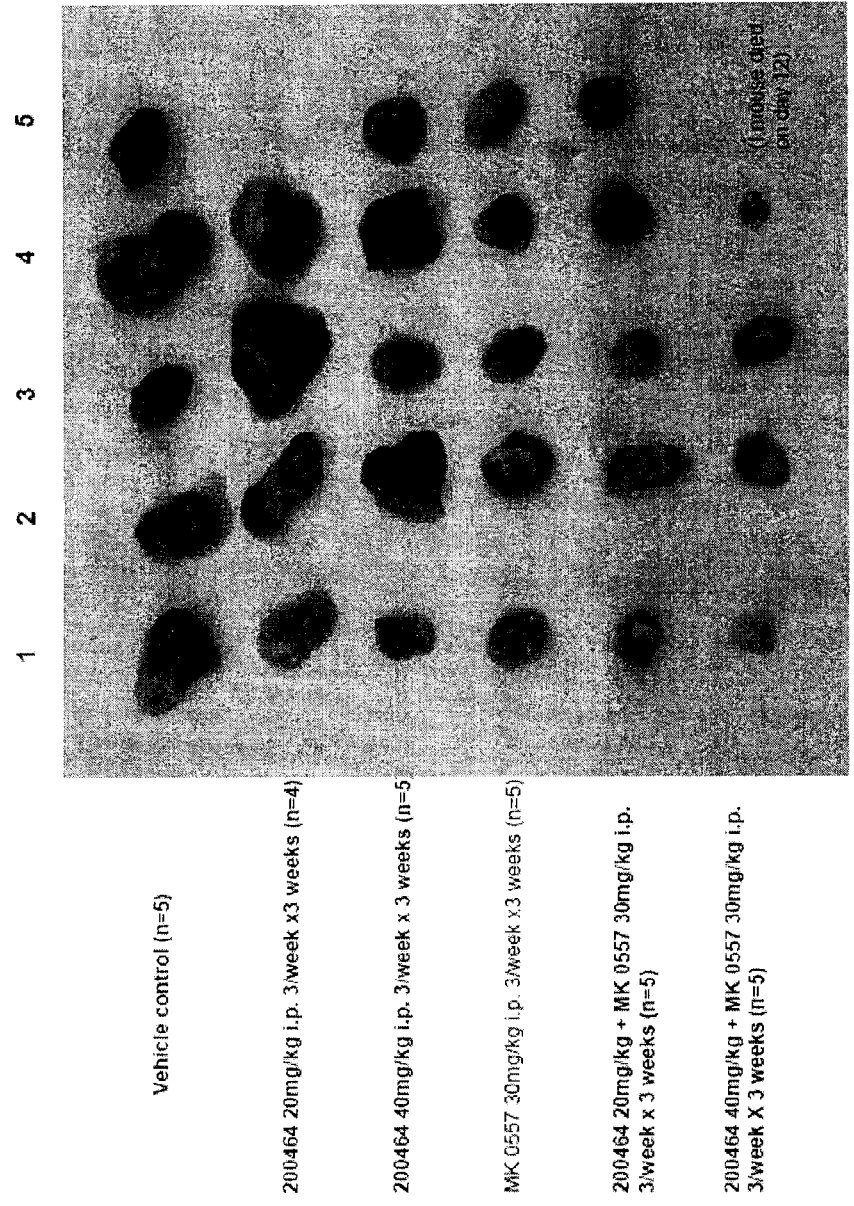
FIG. 21 is a photograph of Hodgkin's lymphoma tumors from a xenograft model treated with selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536), MK-0557 in combination with 200464 (BI2536) or vehicle control.
Figure 22:
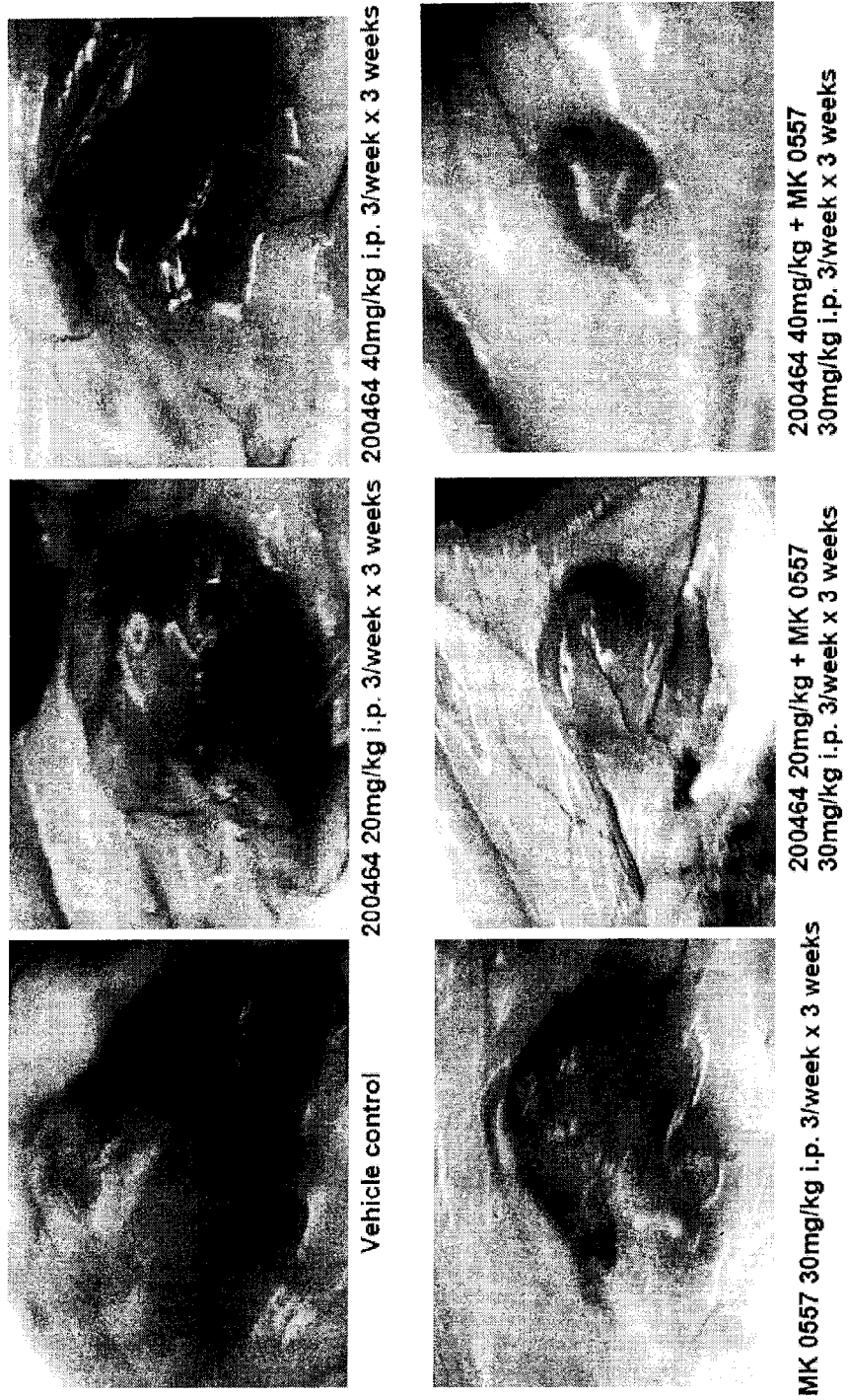
FIG. 22. is a series of photographs depicting the inhibitory effect of selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536) shown together with vehicle control in a xenograft model of Hodgkin's lymphoma.

The inhibitory effect of MK0557 and 200464 in xenograft model of Hodgkin's Lymphoma by tumor weight is shown in FIG. 20. In group 2, the mean tumor weight was 0.8788+/−0.2674 g versus 0.9292+/−0.2763 g for vehicle with an inhibition rate of 5.42%. In group 3, the mean tumor weight was 0.5472+/−0.2097 g versus 0.9292+/−0.2763 g for vehicle with an inhibition rate of 41.11%. In group 4, the mean tumor weight was 0.3048+/−0.0696 g versus 0.9292+/−0.2763 g for vehicle with an inhibition rate of 67.30%. In group 5, the mean tumor weight was 0.2732+/−0.0513 g versus 0.9292+/−0.2763 g for vehicle with an inhibition rate of 70.6%. In group 6, the mean tumor weight was 0.1345+/−0.0401 g versus 0.9292+/−0.2763 g for vehicle with an inhibition rate of 85.53%. FIG. 21 that shows the excised tumors for each group. FIG. 22 shows the inhibitory effect of MK0557 and 200464 of the tumors for the different groups.

Figure 23:
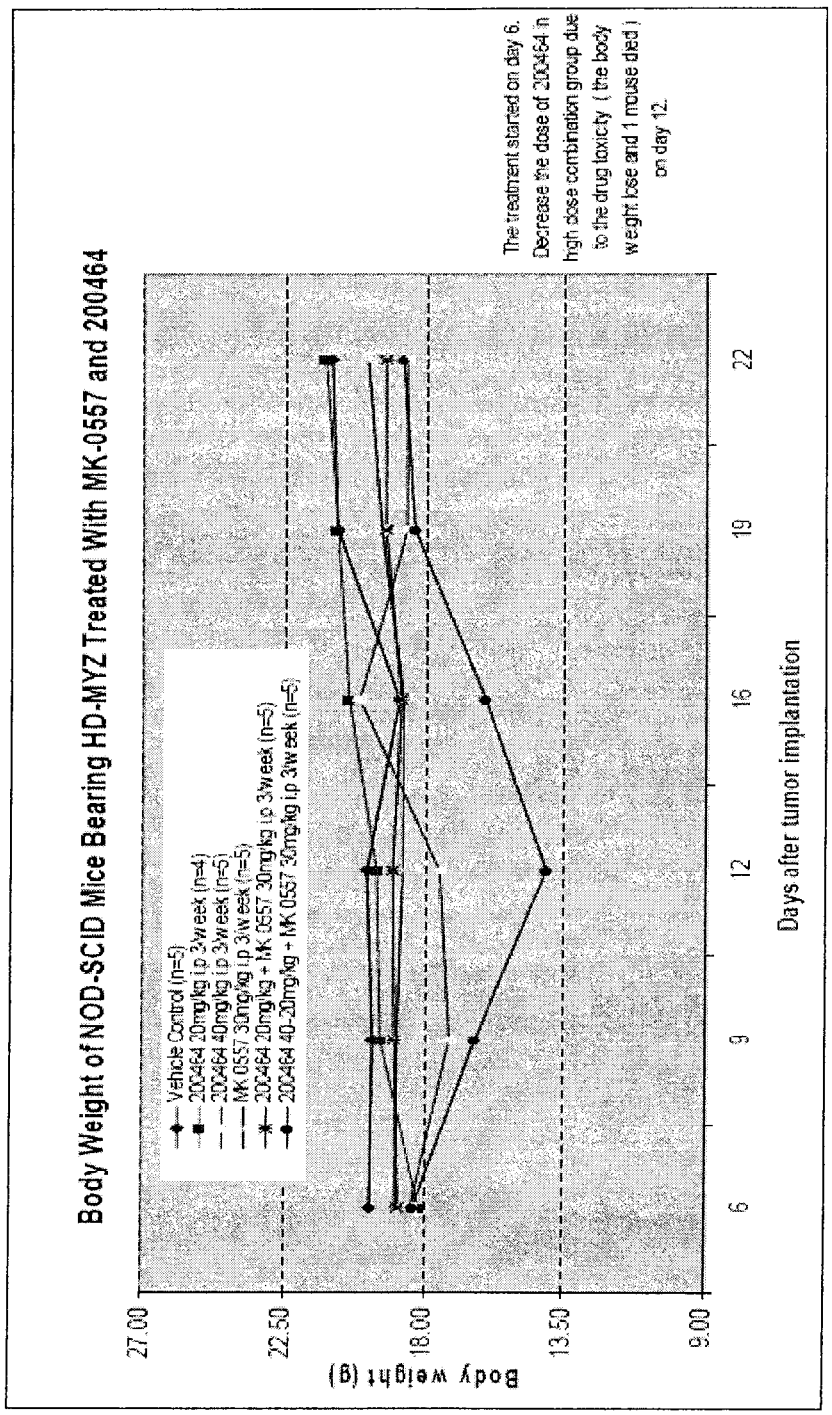
FIG. 23 is a graph illustrating drug toxicity of selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536) in the Hodgkin's Lymphoma xenograft model as depicted by mice body weight.

The doses of the drugs (MK0557 and 200464) were shown to be well tolerated by the mice except in the combination of 40 mg/kg of 200464 and MK557 (group 6). This group showed severe toxicity including one death and an average body weight loss of 23% of total body weight. After decreasing the dose of 200464 to 20 mg/kg, the body weight of the mice in this group recovered. See FIG. 23.

Comparing Liver Weight (g) and Spleen Weight (g)

Figure 24:
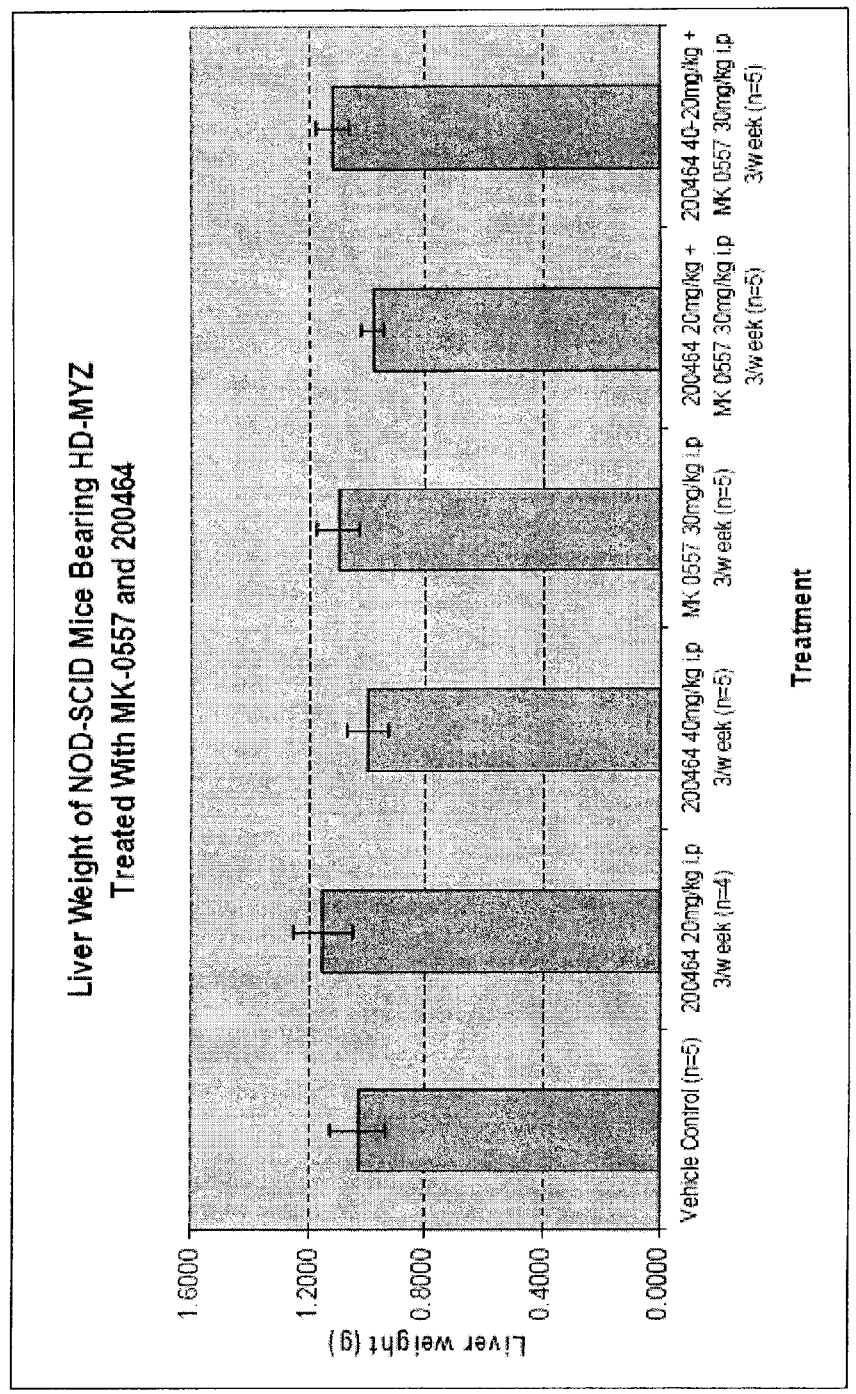
FIG. 24 is a bar graph illustrating the effect of selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536) on liver weight of a Hodgkin's Lymphoma xenograft model.
Figure 25:
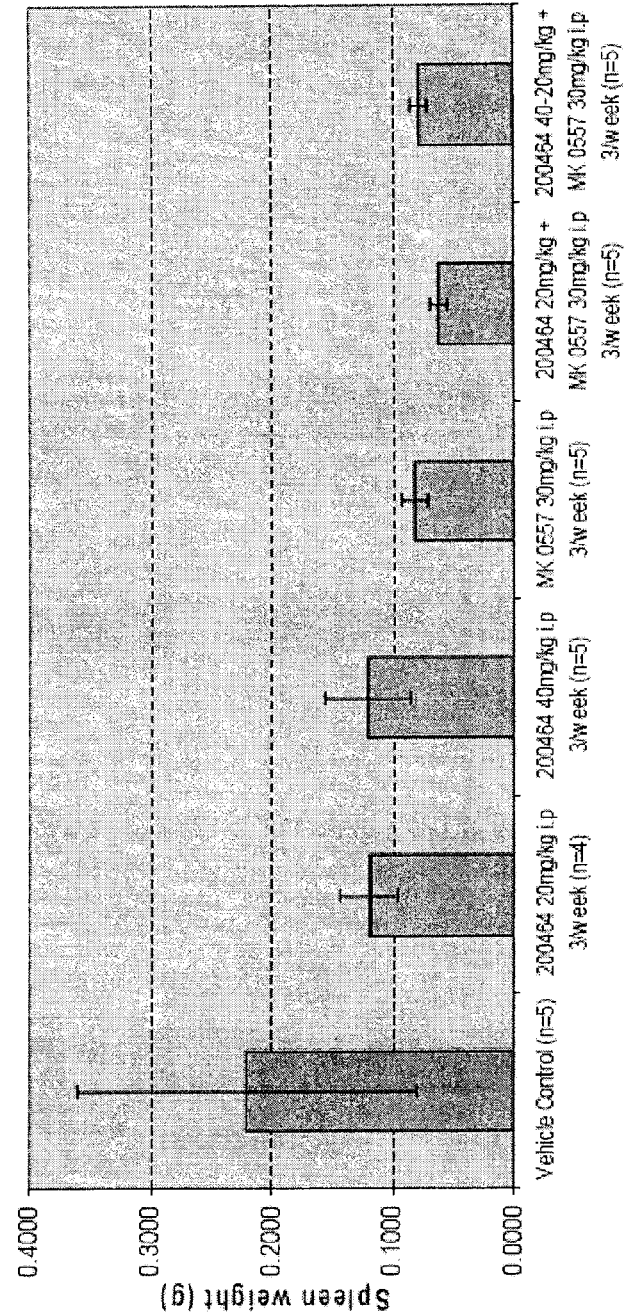
FIG. 25 is a bar graph illustrating the effect of selective NPY5R antagonist MK-0557 (trans-N-[1-(2-fluorophenyl)-3-pyrazolyl]-3-oxospiro[6 azaisobenzofuran-1(3H), 1'-cyclohexane]-4'carboxamide), 200464 (BI2536) or MK-0557 in combination with 200464 (BI2536) on spleen weight of a Hodgkin's Lymphoma xenograft model.

The liver weight of the mice were determined and the results are shown in FIG. 24. No significant effect on liver weight was observed. The spleen weight of the mice in each group were determined and the results are shown in FIG. 25. As shown in FIG. 25, the spleen size is normalized, which indicates efficacy.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating cancer in a subject in need thereof, consisting of administering to said subject a therapeutically effective amount of trans-N-[1-(2-fluorophenyl)-3-pyrazolyl]-3-oxospiro[6 azaisobenzofuran-1(3H), 1'-cyclohexane]-4'carboxamide or a pharmaceutically acceptable salt thereof and optionally, an anticancer chemotherapeutic agent.

2. The method of claim 1, wherein said cancer is selected from the group consisting of carcinoma, sarcoma, melanoma, fibrosarcoma, neuroblastoma, rabdomyosarcoma, lymphoma, myeloid cancer, endothelial cancer, epithelial cancer, breast cancer, cervical cancer, colon cancer, bladder cancer, skin cancer, prostate cancer, brain cancer, endometrial cancer, ovarian cancer, lung cancer, and kidney cancer.

3. A method of treating breast cancer, lung cancer, brain cancer, prostate cancer, or colon cancer in a subject in need thereof, consisting of administering to said subject a therapeutically effective amount of trans-N-[1-(2-fluorophenyl)-3-pyrazolyl]-3-oxospiro[6 azaisobenzofuran-1(3H), 1'-cyclohexane]-4'carboxamide or a pharmaceutically acceptable salt thereof and optionally, an anticancer chemotherapeutic agent.

4. A method of treating cancer in a subject in need thereof, comprising administering to said subject a therapeutically effective amount of an anticancer chemotherapeutic agent and a therapeutically effective amount of trans-N-[1-(2-fluorophenyl)-3-pyrazolyl]-3-oxospiro[6 azaisobenzofuran-1 (3H), 1'-cyclohexane]-4'carboxamide or a pharmaceutically acceptable salt thereof, wherein the anticancer chemotherapeutic agent is 5-FU or 200464 (B1 2536).

5. The method of claim 4, wherein said cancer is selected from the group consisting of carcinoma, sarcoma, melanoma, fibrosarcoma, neuroblastoma, rabdomyosarcoma, lymphoma, myeloid cancer, endothelial cancer, epithelial cancer, breast cancer, cervical cancer, colon cancer, bladder cancer, skin cancer, prostate cancer, brain cancer, endometrial cancer, ovarian cancer, lung cancer and kidney cancer.

6. The method of claim 1 wherein the cancer is Hodgkin's Lymphoma.

7. The method of claim 4, wherein the compound or the pharmaceutically acceptable salt thereof and the anticancer chemotherapeutic agent are administered separately.

8. The method of claim 4, wherein the compound or the pharmaceutically acceptable salt thereof and the anticancer chemotherapeutic agent are administered simultaneously.

9. The method of claim 1, wherein the compound or the pharmaceutically acceptable salt thereof and the optional anticancer chemotherapeutic agent are administered separately.

10. The method of claim 1, wherein the compound or the pharmaceutically acceptable salt thereof and the optional anticancer chemotherapeutic agent are administered simultaneously.

11. The method of claim 4, wherein said cancer is breast cancer, lung cancer, brain cancer, prostate cancer, or colon cancer.

* * * * *